United States Patent
Kim

(10) Patent No.: US 10,294,512 B2
(45) Date of Patent: May 21, 2019

(54) METHOD AND APPARATUS FOR ANALYZING BIOMOLECULES BY USING OLIGONUCLEOTIDE

(71) Applicant: Sung-Chun Kim, Seoul (KR)

(72) Inventor: Sung-Chun Kim, Seoul (KR)

(*) Notice: Subject to any disclaimer, the term of this patent is extended or adjusted under 35 U.S.C. 154(b) by 310 days.

(21) Appl. No.: 15/031,008

(22) PCT Filed: Oct. 21, 2014

(86) PCT No.: PCT/KR2014/009870
§ 371 (c)(1),
(2) Date: Jul. 18, 2016

(87) PCT Pub. No.: WO2015/060609
PCT Pub. Date: Apr. 30, 2015

(65) Prior Publication Data
US 2016/0319330 A1 Nov. 3, 2016

(30) Foreign Application Priority Data

Oct. 21, 2013 (KR) .................... 10-2013-0125087
Nov. 25, 2013 (KR) .................... 10-2013-0143495

(51) Int. Cl.
*C12Q 1/68* (2018.01)
*G01N 33/53* (2006.01)
*C12Q 1/6806* (2018.01)
*C12Q 1/6837* (2018.01)

(52) U.S. Cl.
CPC ......... *C12Q 1/6806* (2013.01); *C12Q 1/6837* (2013.01)

(58) Field of Classification Search
USPC .............. 435/6.1, 6.11, 6.12, 7.1, 91.1, 91.2, 435/91.51; 436/94, 501; 536/23.1, 24.3, 536/24.33, 25.3
See application file for complete search history.

(56) References Cited

FOREIGN PATENT DOCUMENTS

| JP | 2006-500033 | 1/2006 | |
|---|---|---|---|
| JP | 2009-521946 | 6/2009 | |
| JP | 2009-528054 | 8/2009 | |
| JP | 2012-506712 | 3/2012 | |
| WO | WO 2001/036585 | 5/2001 | .............. C12M 1/34 |
| WO | WO 2011162894 | 12/2011 | .............. C12Q 1/68 |
| WO | WO 2012/106525 | 8/2012 | |

OTHER PUBLICATIONS

Extended European Search Report, dated Mar. 22, 2017, in European Patent Application No. EP 14855536.0.
Japanese Office Action, dated Aug. 1, 2017, in Japanese Patent Application No. JP 2016-526155.

*Primary Examiner* — Frank W Lu
(74) *Attorney, Agent, or Firm* — Harness, Dickey & Pierce, P.L.C.

(57) ABSTRACT

The present invention relates to a method for analyzing biomolecules by using an oligonucleotide, and specifically, provides a method and an apparatus for determining the meaning of biomolecules in a biosample by analyzing through one examination of the biomolecules contained in the biosample by preparing, with respect to a nucleic acid including a target nucleic acid such as nucleic acid and receptor-analysis ligand conjugates, an oligonucleotide, which complementarily binds completely to a specific region of the target nucleic acid, and analyzing the target nucleic acid.

13 Claims, 8 Drawing Sheets
Specification includes a Sequence Listing.

| β-actin mRNA_1 | β-actin mRNA_2 | IL17 mRNA_1 | IL17 mRNA_2 | IL17RA mRNA_1 | IL17RA mRNA_2 |
|---|---|---|---|---|---|
| IL17 SNP_1 | IL17 SNP_2 | IL17 SNP_3 | IL17 SNP_4 | IL17 SNP_5 | IL17 SNP_6 |
| IL17 SNP_7 | IL17 SNP_8 | IL17 SNP_9 | IL17 SNP_10 | IL17 SNP_11 | IL17RA SNP_1 |
| IL17RA SNP_2 | IL17RA SNP_3 | IL17RA SNP_4 | IL17RA SNP_5 | IL17RA SNP_6 | IL17RA SNP_7 |
| IL17RA SNP_8 | IL17RA SNP_9 | IL17RA SNP_10 | IL17RA SNP_11 | IL17RA SNP_12 | IL17RA SNP_13 |
| IL17RA SNP_14 | IL17 APTAMER | IL17RA APTAMER | IL17 METHYLATED | - | - |

FIG. 7

```
                           SEQUENCE LISTING

<160> NUMBER OF SEQ ID NOS: 188

<210> SEQ ID NO 1
<211> LENGTH: 25
<212> TYPE: DNA
<213> ORGANISM: Artificial Sequence
<220> FEATURE:
<223> OTHER INFORMATION: Upstream Oligonucleotide

<400> SEQUENCE: 1
gggcgacgag gcccagagca agaga                                           25

<210> SEQ ID NO 2
<211> LENGTH: 25
<212> TYPE: DNA
<213> ORGANISM: Artificial Sequence
<220> FEATURE:
<223> OTHER INFORMATION: Upstream Oligonucleotide

<400> SEQUENCE: 2
cagatcatgt ttgagacctt caaca                                           25

<210> SEQ ID NO 3
<211> LENGTH: 25
<212> TYPE: DNA
<213> ORGANISM: Artificial Sequence
<220> FEATURE:
<223> OTHER INFORMATION: Upstream Oligonucleotide

<400> SEQUENCE: 3
ccctcaggaa ccctcatcct tcaaa                                           25

<210> SEQ ID NO 4
<211> LENGTH: 25
<212> TYPE: DNA
<213> ORGANISM: Artificial Sequence
<220> FEATURE:
<223> OTHER INFORMATION: Upstream Oligonucleotide

<400> SEQUENCE: 4
taaccggaat accaatacca atccc                                           25

<210> SEQ ID NO 5
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 5
gatggcctgc ctgcggctga cctgatt                                         27

<210> SEQ ID NO 6
<211> LENGTH: 25
<212> TYPE: DNA
<213> ORGANISM: Artificial Sequence
<220> FEATURE:
<223> OTHER INFORMATION: Upstream Oligonucleotide

<400> SEQUENCE: 6
gagtacagga taccacaatg cactc                                           25
```

<210> SEQ ID NO 7
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 7
aaactcatcg tgaagtcaaa cattcaa                                          27

<210> SEQ ID NO 8
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 8
aaactcatcg tgaagtcaaa cattcac                                          27

<210> SEQ ID NO 9
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 9
ggaatactgt atatgtagga taggaaa                                          27

<210> SEQ ID NO 10
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 10
ggaatactgt atatgtagga taggaag                                          27

<210> SEQ ID NO 11
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 11
tgtcacccct gaacccactg cgacaca                                          27

<210> SEQ ID NO 12
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 12
tgtcacccct gaacccactg cgacacg                                          27

<210> SEQ ID NO 13
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 13
cccccctgcc cccttttct ccatctc					27

<210> SEQ ID NO 14
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 14
cccccctgcc cccttttct ccatctt					27

<210> SEQ ID NO 15
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 15
tgtattcctg agaaggaact attctca					27

<210> SEQ ID NO 16
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 16
tgtattcctg agaaggaact attctcg					27

<210> SEQ ID NO 17
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 17
tcattggtgg tgagtcctgc actaaca					27

<210> SEQ ID NO 18
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 18
tcattggtgg tgagtcctgc actaacg					27

<210> SEQ ID NO 19
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 19
aacacctggc caaggaatct gtgagga					27

<210> SEQ ID NO 20

-continued

```
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 20
aacacctggc caaggaatct gtgaggg                                              27

<210> SEQ ID NO 21
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 21
caaatgtatt ttgatcattt gacttca                                              27

<210> SEQ ID NO 22
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 22
caaatgtatt ttgatcattt gacttct                                              27

<210> SEQ ID NO 23
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 23
tgggctgaac ttttctcata cttaaaa                                              27

<210> SEQ ID NO 24
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 24
tgggctgaac ttttctcata cttaaag                                              27

<210> SEQ ID NO 25
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 25
ctgcccttcc cattttcctt cagaaga                                              27

<210> SEQ ID NO 26
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 26
```
ctgcccttcc cattttcctt cagaagg                                              27

<210> SEQ ID NO 27
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 27
ctgaactttt ctcatactta aagttca                                              27

<210> SEQ ID NO 28
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 28
ctgaactttt ctcatactta aagttcg                                              27

<210> SEQ ID NO 29
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 29
gatggcctgc ctgcggctga cctgatc                                              27

<210> SEQ ID NO 30
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 30
gatggcctgc ctgcggctga cctgatt                                              27

<210> SEQ ID NO 31
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 31
tggatcatct actcagccga ccacccc                                              27

<210> SEQ ID NO 32
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 32
tggatcatct actcagccga ccaccck                                              27

<210> SEQ ID NO 33
<211> LENGTH: 27
<212> TYPE: DNA

```
<213> ORGANISM: Artificial Sequence
<220> FEATURE:
<223> OTHER INFORMATION: Upstream Oligonucleotide

<400> SEQUENCE: 33
ctgtcactaa ggagttaacc cccgcaa                                              27

<210> SEQ ID NO 34
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 34
ctgtcactaa ggagttaacc cccgcag                                              27

<210> SEQ ID NO 35
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 35
catagtagat agcaatctat tcaacca                                              27

<210> SEQ ID NO 36
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 36
catagtagat agcaatctat tcaaccg                                              27

<210> SEQ ID NO 37
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 37
gcaagttagg attagagggc tgggaca                                              27

<210> SEQ ID NO 38
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 38
gcaagttagg attagagggc tgggacg                                              27

<210> SEQ ID NO 39
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 39
tgggaagtaa cgactctctt aggtgca                                              27
```

<210> SEQ ID NO 40
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 40
tgggaagtaa cgactctctt aggtgcg                                27

<210> SEQ ID NO 41
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 41
gcatgggagg acctatggga ggttcca                                27

<210> SEQ ID NO 42
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 42
gcatgggagg acctatggga ggttccg                                27

<210> SEQ ID NO 43
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 43
atgctatttt ccctttttcc tctgttc                                27

<210> SEQ ID NO 44
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 44
atgctatttt ccctttttcc tctgttt                                27

<210> SEQ ID NO 45
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 45 cacccctct acgtggacgt ggtccta                                 27

<210> SEQ ID NO 46
<211> LENGTH: 27
<212> TYPE: DNA
<213> ORGANISM: Artificial Sequence
<220> FEATURE:

```
<223> OTHER INFORMATION: Upstream Oligonucleotide

<400> SEQUENCE: 46
caccccctct acgtggacgt ggtcctg                                            27

<210> SEQ ID NO 47
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 47
acgctttccc caaccacaat ccttcac                                            27

<210> SEQ ID NO 48
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 48
acgctttccc caaccacaat ccttcag                                            27

<210> SEQ ID NO 49
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 49
tcagcggtgg ggggatcagg tcagcca                                            27

<210> SEQ ID NO 50
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 50
tcagcggtgg ggggatcagg tcagccg                                            27

<210> SEQ ID NO 51
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 51
tggtcggctg agtagatgat ccagacc                                            27

<210> SEQ ID NO 52
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 52
tggtcggctg agtagatgat ccagact                                            27
```

-continued

```
<210> SEQ ID NO 53
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 53
tggtcggctg agtagatgat ccagacc                                         27

<210> SEQ ID NO 54
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 54
tggtcggctg agtagatgat ccagact                                         27

<210> SEQ ID NO 55
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 55
gttctgaggg gtgattaggg aggagac                                         27

<210> SEQ ID NO 56
<211> LENGTH: 27
<212> TYPE: DNA
<213> ORGANISM: Artificial Sequence
<220> FEATURE:
<223> OTHER INFORMATION: Upstream Oligonucleotide

<400> SEQUENCE: 56
gttctgaggg gtgattaggg aggagag                                         27

<210> SEQ ID NO 57
<211> LENGTH: 18
<212> TYPE: RNA
<213> ORGANISM: Artificial Sequence
<220> FEATURE:
<223> OTHER INFORMATION: Aptamer

<400> SEQUENCE: 57
ggucuagccg gaggaguc                                                   18

<210> SEQ ID NO 58
<211> LENGTH: 15
<212> TYPE: DNA
<213> ORGANISM: Artificial Sequence
<220> FEATURE:
<223> OTHER INFORMATION: Upstream Oligonucleotide

<400> SEQUENCE: 58
acgcgctagg atcaa                                                      15

<210> SEQ ID NO 59
<211> LENGTH: 31
<212> TYPE: DNA
<213> ORGANISM: Artificial Sequence
<220> FEATURE:
<223> OTHER INFORMATION: Upstream Oligonucleotide
```

```
<400> SEQUENCE: 59
tcaaatcaat tttaacatta tctacaacaa g                                    31

<210> SEQ ID NO 60
<211> LENGTH: 31
<212> TYPE: DNA
<213> ORGANISM: Artificial Sequence
<220> FEATURE:
<223> OTHER INFORMATION: Upstream Oligonucleotide

<400> SEQUENCE: 60
tcaaatcaat tttaacatta tctacaacaa a                                    31

<210> SEQ ID NO 61
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 61
ggcatcctca ccctgaagta cccca                                           25

<210> SEQ ID NO 62
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 62
ccccagccat gtacgttgct atcca                                           25

<210> SEQ ID NO 63
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 63
gacagcctca tttcggacta aactc                                           25

<210> SEQ ID NO 64
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 64
aaaaggtcct cagattacta caacc                                           25

<210> SEQ ID NO 65
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 65 cctttgggc tcagtctctc caata                                            25

<210> SEQ ID NO 66
<211> LENGTH: 25
```

<212> TYPE: DNA
<213> ORGANISM: Artificial Sequence
<220> FEATURE:
<223> OTHER INFORMATION: Downstream Oligonucleotide

<400> SEQUENCE: 66
ttcctgcgta gagcacatgt tccca                                              25

<210> SEQ ID NO 67
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 67
attggaagaa agagctatag aaaat                                              25

<210> SEQ ID NO 68
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 68
tgaaagcttt ggtaggtatt taagt                                              25

<210> SEQ ID NO 69
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 69
ccacgtaagt gaccacagaa ggaga                                              25

<210> SEQ ID NO 70
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 70
catcaccttt gtccagtctc tatcc                                              25

<210> SEQ ID NO 71
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 71
aggacctgag tccaagttca tctta                                              25

<210> SEQ ID NO 72
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 72
tgcgatgctc ttgctgattt ggacc					25

<210> SEQ ID NO 73
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 73
aaagaaagat caaatggaaa atcaa					25

<210> SEQ ID NO 74
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 74
tacaaataag tctctgttct gtgga					25

<210> SEQ ID NO 75
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 75
ttcgttctgc cccatcagct ccttt					25

<210> SEQ ID NO 76
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 76
agagattctt ctatgacctc attgg					25

<210> SEQ ID NO 77
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 77
ttctgcccca tcagctcctt tctgg					25

<210> SEQ ID NO 78
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 78
cccccaccgc tgaagcccag gaagg					25

<210> SEQ ID NO 79
<211> LENGTH: 25
<212> TYPE: DNA
<213> ORGANISM: Artificial Sequence

```
<220> FEATURE:
<223> OTHER INFORMATION: Downstream Oligonucleotide

<400> SEQUENCE: 79
ctctacgtgg acgtggtcct gaaat                                              25

<210> SEQ ID NO 80
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 80
agcagttttt tcatcacatc tctga                                              25

<210> SEQ ID NO 81
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 81
tttctagttt gatggacatt tagat                                              25

<210> SEQ ID NO 82
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 82
tttagcccca cccctttacc catca                                              25

<210> SEQ ID NO 83
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 83
gctgggacac agtctcacag accag                                              25

<210> SEQ ID NO 84
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 84
ataacattca gtagcatctc ggcca                                              25

<210> SEQ ID NO 85
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 85
tcattgcaga accaattccg ggtaa                                              25
```

```
<210> SEQ ID NO 86
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 86
aaattcgccc agttcctgct caccg                                         25

<210> SEQ ID NO 87
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 87
ctcaggcatc tcctcgggga tcccc                                         25

<210> SEQ ID NO 88
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 88
caggcaggcc atctaaggaa acaag                                         25

<210> SEQ ID NO 89
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 89
ttcctgggct tcagcggtgg gggga                                         25

<210> SEQ ID NO 90
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 90
ttcctgggct tcagcggtgg gggga                                         25

<210> SEQ ID NO 91
<211> LENGTH: 25
<212> TYPE: DNA
<213> ORGANISM: Artificial Sequence
<220> FEATURE:
<223> OTHER INFORMATION: Downstream Oligonucleotide

<400> SEQUENCE: 91
tttagtttaa cttggagtcc ttcag                                         25

<210> SEQ ID NO 92
<211> LENGTH: 15
<212> TYPE: RNA
<213> ORGANISM: Artificial Sequence
<220> FEATURE:
<223> OTHER INFORMATION: Aptamer
```

```
<400> SEQUENCE: 92
aguaaucggu agacc                                                    15

<210> SEQ ID NO 93
<211> LENGTH: 15
<212> TYPE: DNA
<213> ORGANISM: Artificial Sequence
<220> FEATURE:
<223> OTHER INFORMATION: Downstream Oligonucleotide

<400> SEQUENCE: 93
agctgcactg aagtg                                                    15

<210> SEQ ID NO 94
<211> LENGTH: 30
<212> TYPE: DNA
<213> ORGANISM: Artificial Sequence
<220> FEATURE:
<223> OTHER INFORMATION: Downstream Oligonucleotide

<400> SEQUENCE: 94
gtcatacttg tgggctggag accaaaagcc                                    30

<210> SEQ ID NO 95
<211> LENGTH: 24
<212> TYPE: DNA
<213> ORGANISM: Artificial Sequence
<220> FEATURE:
<223> OTHER INFORMATION: Capture probe

<400> SEQUENCE: 95
gatttgtatt gattgagatt aaag                                          24

<210> SEQ ID NO 96
<211> LENGTH: 24
<212> TYPE: DNA
<213> ORGANISM: Artificial Sequence
<220> FEATURE:
<223> OTHER INFORMATION: Capture probe

<400> SEQUENCE: 96
tgattgtagt atgtattgat aaag                                          24

<210> SEQ ID NO 97
<211> LENGTH: 24
<212> TYPE: DNA
<213> ORGANISM: Artificial Sequence
<220> FEATURE:
<223> OTHER INFORMATION: Capture probe

<400> SEQUENCE: 97
gattgtaaga tttgataaag tgta                                          24

<210> SEQ ID NO 98
<211> LENGTH: 24
<212> TYPE: DNA
<213> ORGANISM: Artificial Sequence
<220> FEATURE:
<223> OTHER INFORMATION: Capture probe

<400> SEQUENCE: 98
gatttgaaga ttattggtaa tgta                                          24

<210> SEQ ID NO 99
```

```
<211> LENGTH: 24
<212> TYPE: DNA
<213> ORGANISM: Artificial Sequence
<220> FEATURE:
<223> OTHER INFORMATION: Capture probe

<400> SEQUENCE: 99
gattgattat tgtgatttga attg                                          24

<210> SEQ ID NO 100
<211> LENGTH: 24
<212> TYPE: DNA
<213> ORGANISM: Artificial Sequence
<220> FEATURE:
<223> OTHER INFORMATION: Capture probe

<400> SEQUENCE: 100
gatttgattg taaagattg ttga                                           24

<210> SEQ ID NO 101
<211> LENGTH: 24
<212> TYPE: DNA
<213> ORGANISM: Artificial Sequence
<220> FEATURE:
<223> OTHER INFORMATION: Capture probe

<400> SEQUENCE: 101
attggtaaat tgtaaatga attg                                           24

<210> SEQ ID NO 102
<211> LENGTH: 24
<212> TYPE: DNA
<213> ORGANISM: Artificial Sequence
<220> FEATURE:
<223> OTHER INFORMATION: Capture probe

<400> SEQUENCE: 102
gtaagtaatg aatgtaaaag gatt                                          24

<210> SEQ ID NO 103
<211> LENGTH: 24
<212> TYPE: DNA
<213> ORGANISM: Artificial Sequence
<220> FEATURE:
<223> OTHER INFORMATION: Capture probe

<400> SEQUENCE: 103
gtaagatgtt gatatagaag atta                                          24

<210> SEQ ID NO 104
<211> LENGTH: 24
<212> TYPE: DNA
<213> ORGANISM: Artificial Sequence
<220> FEATURE:
<223> OTHER INFORMATION: Capture probe

<400> SEQUENCE: 104
tgtagatttg tatgtatgta tgat                                          24

<210> SEQ ID NO 105
<211> LENGTH: 24
<212> TYPE: DNA
<213> ORGANISM: Artificial Sequence
<220> FEATURE:
<223> OTHER INFORMATION: Capture probe

<400> SEQUENCE: 105
```

-continued gattaaagtg attgatgatt tgta                                      24

<210> SEQ ID NO 106
<211> LENGTH: 24
<212> TYPE: DNA
<213> ORGANISM: Artificial Sequence
<220> FEATURE:
<223> OTHER INFORMATION: Capture probe

<400> SEQUENCE: 106
aaagaaagaa agaaagaaag tgta                                      24

<210> SEQ ID NO 107
<211> LENGTH: 24
<212> TYPE: DNA
<213> ORGANISM: Artificial Sequence
<220> FEATURE:
<223> OTHER INFORMATION: Capture probe

<400> SEQUENCE: 107
ttagtgaaga agtatagttt attg                                      24

<210> SEQ ID NO 108
<211> LENGTH: 24
<212> TYPE: DNA
<213> ORGANISM: Artificial Sequence
<220> FEATURE:
<223> OTHER INFORMATION: Capture probe

<400> SEQUENCE: 108
aaagtaagtt aagatgtata gtag                                      24

<210> SEQ ID NO 109
<211> LENGTH: 24
<212> TYPE: DNA
<213> ORGANISM: Artificial Sequence
<220> FEATURE:
<223> OTHER INFORMATION: Capture probe

<400> SEQUENCE: 109
tgaattgatg aatgaatgaa gtat                                      24

<210> SEQ ID NO 110
<211> LENGTH: 24
<212> TYPE: DNA
<213> ORGANISM: Artificial Sequence
<220> FEATURE:
<223> OTHER INFORMATION: Capture probe

<400> SEQUENCE: 110
tgatgatttg aatgaagatt gatt                                      24

<210> SEQ ID NO 111
<211> LENGTH: 24
<212> TYPE: DNA
<213> ORGANISM: Artificial Sequence
<220> FEATURE:
<223> OTHER INFORMATION: Capture probe

<400> SEQUENCE: 111
tgataaagtg ataaaggatt aaag                                      24

<210> SEQ ID NO 112
<211> LENGTH: 24
<212> TYPE: DNA

<213> ORGANISM: Artificial Sequence
<220> FEATURE:
<223> OTHER INFORMATION: Capture probe

<400> SEQUENCE: 112
tgatttgagt atttgagatt ttga                                          24

<210> SEQ ID NO 113
<211> LENGTH: 24
<212> TYPE: DNA
<213> ORGANISM: Artificial Sequence
<220> FEATURE:
<223> OTHER INFORMATION: Capture probe

<400> SEQUENCE: 113
gtatttgagt aagtaattga ttga                                          24

<210> SEQ ID NO 114
<211> LENGTH: 24
<212> TYPE: DNA
<213> ORGANISM: Artificial Sequence
<220> FEATURE:
<223> OTHER INFORMATION: Capture probe

<400> SEQUENCE: 114
gattgtattg aagtattgta aaag                                          24

<210> SEQ ID NO 115
<211> LENGTH: 24
<212> TYPE: DNA
<213> ORGANISM: Artificial Sequence
<220> FEATURE:
<223> OTHER INFORMATION: Capture probe

<400> SEQUENCE: 115
tgatttgaga ttaaagaaag gatt                                          24

<210> SEQ ID NO 116
<211> LENGTH: 24
<212> TYPE: DNA
<213> ORGANISM: Artificial Sequence
<220> FEATURE:
<223> OTHER INFORMATION: Capture probe

<400> SEQUENCE: 116
tgattgaatt gagtaaaaag gatt                                          24

<210> SEQ ID NO 117
<211> LENGTH: 24
<212> TYPE: DNA
<213> ORGANISM: Artificial Sequence
<220> FEATURE:
<223> OTHER INFORMATION: Capture probe

<400> SEQUENCE: 117
aaagttgaga tttgaatgat tgaa                                          24

<210> SEQ ID NO 118
<211> LENGTH: 24
<212> TYPE: DNA
<213> ORGANISM: Artificial Sequence
<220> FEATURE:
<223> OTHER INFORMATION: Capture probe

<400> SEQUENCE: 118
gtattgtatt gaaaaggtaa ttga                                          24

<210> SEQ ID NO 119
<211> LENGTH: 24
<212> TYPE: DNA
<213> ORGANISM: Artificial Sequence
<220> FEATURE:
<223> OTHER INFORMATION: Capture probe

<400> SEQUENCE: 119
tgaagatttg aagtaattga aaag                                            24

<210> SEQ ID NO 120
<211> LENGTH: 24
<212> TYPE: DNA
<213> ORGANISM: Artificial Sequence
<220> FEATURE:
<223> OTHER INFORMATION: Capture probe

<400> SEQUENCE: 120
tgaaaaagtg tagattttga gtaa                                            24

<210> SEQ ID NO 121
<211> LENGTH: 24
<212> TYPE: DNA
<213> ORGANISM: Artificial Sequence
<220> FEATURE:
<223> OTHER INFORMATION: Capture probe

<400> SEQUENCE: 121
aaagttgagt attgatttga aaag                                            24

<210> SEQ ID NO 122
<211> LENGTH: 24
<212> TYPE: DNA
<213> ORGANISM: Artificial Sequence
<220> FEATURE:
<223> OTHER INFORMATION: Capture probe

<400> SEQUENCE: 122
ttgataatgt ttgtttgttt gtag                                            24

<210> SEQ ID NO 123
<211> LENGTH: 24
<212> TYPE: DNA
<213> ORGANISM: Artificial Sequence
<220> FEATURE:
<223> OTHER INFORMATION: Capture probe

<400> SEQUENCE: 123
aaagaaagga tttgtagtaa gatt                                            24

<210> SEQ ID NO 124
<211> LENGTH: 24
<212> TYPE: DNA
<213> ORGANISM: Artificial Sequence
<220> FEATURE:
<223> OTHER INFORMATION: Capture probe

<400> SEQUENCE: 124
gtaaaaagaa aggtataaag gtaa                                            24

<210> SEQ ID NO 125
<211> LENGTH: 24
<212> TYPE: DNA
<213> ORGANISM: Artificial Sequence
<220> FEATURE:

```
<223> OTHER INFORMATION: Capture probe

<400> SEQUENCE: 125
gattaaagtt gattgaaaag tgaa                                        24

<210> SEQ ID NO 126
<211> LENGTH: 24
<212> TYPE: DNA
<213> ORGANISM: Artificial Sequence
<220> FEATURE:
<223> OTHER INFORMATION: Capture probe

<400> SEQUENCE: 126
gtagattagt ttgaagtgaa taat                                        24

<210> SEQ ID NO 127
<211> LENGTH: 24
<212> TYPE: DNA
<213> ORGANISM: Artificial Sequence
<220> FEATURE:
<223> OTHER INFORMATION: Capture probe

<400> SEQUENCE: 127
aaaggattaa agtgaagtaa ttga                                        24

<210> SEQ ID NO 128
<211> LENGTH: 24
<212> TYPE: DNA
<213> ORGANISM: Artificial Sequence
<220> FEATURE:
<223> OTHER INFORMATION: Capture probe

<400> SEQUENCE: 128
tgaaatgaat gaatgatgaa attg                                        24

<210> SEQ ID NO 129
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 129
ctttaatctc aatcaataca aatc                                        24

<210> SEQ ID NO 130
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 130
ctttatcaat acatactaca atca                                        24

<210> SEQ ID NO 131
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 131
tacactttat caaatcttac aatc                                        24
```

```
<210> SEQ ID NO 132
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 132
tacattacca ataatcttca aatc                                            24

<210> SEQ ID NO 133
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 133
caattcaaat cacaataatc aatc                                            24

<210> SEQ ID NO 134
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 134
tcaacaatct tttacaatca aatc                                            24

<210> SEQ ID NO 135
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 135
caattcattt accaatttac caat                                            24

<210> SEQ ID NO 136
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 136 aatccttta cattcattac ttac                                             24

<210> SEQ ID NO 137
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 137
taatcttcta tatcaacatc ttac                                            24

<210> SEQ ID NO 138
<211> LENGTH: 24
<212> TYPE: DNA
<213> ORGANISM: Artificial Sequence
<220> FEATURE:
<223> OTHER INFORMATION: Complementary sequence of Capture probe
```

```
<400> SEQUENCE: 138
atcatacata catacaaatc taca                                          24

<210> SEQ ID NO 139
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 139
tacaaatcat catcactttt aatc                                          24

<210> SEQ ID NO 140
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 140
tacactttct ttctttcttt cttt                                          24

<210> SEQ ID NO 141
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 141
caataaacta tacttcttca ctaa                                          24

<210> SEQ ID NO 142
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 142
ctactataca tcttactata cttt                                          24

<210> SEQ ID NO 143
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 143
atacttcatt cattcatcaa ttca                                          24

<210> SEQ ID NO 144
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 144
aatcaatctt cattcaaatc atca                                          24

<210> SEQ ID NO 145
<211> LENGTH: 24
```

```
<212> TYPE: DNA
<213> ORGANISM: Artificial Sequence
<220> FEATURE:
<223> OTHER INFORMATION: Complementary sequence of Capture probe

<400> SEQUENCE: 145
ctttaatcct ttatcacttt atca                                            24

<210> SEQ ID NO 146
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 146
tcaaaatctc aaatactcaa atca                                            24

<210> SEQ ID NO 147
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 147
tcaatcaatt acttactcaa atag                                            24

<210> SEQ ID NO 148
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 148
cttttacaat acttcaatac aatc                                            24

<210> SEQ ID NO 149
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 149
aatcctttct ttaatctcaa atca                                            24

<210> SEQ ID NO 150
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 150 aatcctttttt actcaattca atca                                           24

<210> SEQ ID NO 151
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 151
```
ttcaatcatt caaatctcaa cttt                                              24

<210> SEQ ID NO 152
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 152
tcaattacct tttcaataca atac                                              24

<210> SEQ ID NO 153
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 153
cttttcaatt acttcaaatc ttca                                              24

<210> SEQ ID NO 154
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 154
ttactcaaaa tctcactttt ttca                                              24

<210> SEQ ID NO 155
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 155
cttttcaaat caatactcaa cttt                                              24

<210> SEQ ID NO 156
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 156
ctacaaacaa acaaacatta tcaa                                              24

<210> SEQ ID NO 157
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 157
aatcttacta caaatccttt cttt                                              24

<210> SEQ ID NO 158
<211> LENGTH: 24
<212> TYPE: DNA
<213> ORGANISM: Artificial Sequence

```
<220> FEATURE:
<223> OTHER INFORMATION: Complementary sequence of Capture probe

<400> SEQUENCE: 158
ttacctttat acctttcttt ttac                                          24

<210> SEQ ID NO 159
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 159
ttcacttttc aatcaacttt aatc                                          24

<210> SEQ ID NO 160
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 160
attattcact tcaaactaat ctac                                          24

<210> SEQ ID NO 161
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 161
tcaattactt cactttaatc cttt                                          24

<210> SEQ ID NO 162
<211> LENGTH: 24
<212> TYPE: DNA
<213> ORGANISM: Artificial Sequence
<220> FEATURE:
<223> OTHER INFORMATION: Complementary sequence of Capture probe

<400> SEQUENCE: 162
caatttcatc attcattcat ttca                                          24

<210> SEQ ID NO 163
<211> LENGTH: 18
<212> TYPE: DNA
<213> ORGANISM: Artificial Sequence
<220> FEATURE:
<223> OTHER INFORMATION: Primer

<400> SEQUENCE: 163
acttcgtcag taacggac                                                 18

<210> SEQ ID NO 164
<211> LENGTH: 18
<212> TYPE: DNA
<213> ORGANISM: Artificial Sequence
<220> FEATURE:
<223> OTHER INFORMATION: Primer

<400> SEQUENCE: 164
gagtcgaggt catatcgt                                                 18
```

<210> SEQ ID NO 165
<211> LENGTH: 18
<212> TYPE: DNA
<213> ORGANISM: Artificial Sequence
<220> FEATURE:
<223> OTHER INFORMATION: Primer

<400> SEQUENCE: 165
gtctgcctat agtgagtc                                                 18

<210> SEQ ID NO 166
<211> LENGTH: 33
<212> TYPE: RNA
<213> ORGANISM: Artificial Sequence
<220> FEATURE:
<223> OTHER INFORMATION: Aptamer

<400> SEQUENCE: 166
ggucuagccg gaggagucag uaaucgguag acc                                33

<210> SEQ ID NO 167
<211> LENGTH: 30
<212> TYPE: DNA
<213> ORGANISM: Artificial Sequence
<220> FEATURE:
<223> OTHER INFORMATION: Aptamer

<400> SEQUENCE: 167
acgcgctagg atcaaagctg cactgaagtg                                    30

<210> SEQ ID NO 168
<211> LENGTH: 30
<212> TYPE: DNA
<213> ORGANISM: Artificial Sequence
<220> FEATURE:
<223> OTHER INFORMATION: Upstream Oligonucleotide

<400> SEQUENCE: 168
gcagcactgc ataattctct tactgtcatg                                    30

<210> SEQ ID NO 169
<211> LENGTH: 30
<212> TYPE: DNA
<213> ORGANISM: Artificial Sequence
<220> FEATURE:
<223> OTHER INFORMATION: Upstream Oligonucleotide

<400> SEQUENCE: 169
gcagcactgc ataattctct tactgtcata                                    30

<210> SEQ ID NO 170
<211> LENGTH: 30
<212> TYPE: DNA
<213> ORGANISM: Artificial Sequence
<220> FEATURE:
<223> OTHER INFORMATION: Downstream Oligonucleotide

<400> SEQUENCE: 170
ccatccgtaa gatgcttttc tgtgactggt                                    30

<210> SEQ ID NO 171
<211> LENGTH: 40
<212> TYPE: RNA
<213> ORGANISM: Artificial Sequence
<220> FEATURE:
<223> OTHER INFORMATION: Aptamer

```
<400> SEQUENCE: 171
cgcaguuugc gcgcguucca aguucucuca ucacggaaua                                40

<210> SEQ ID NO 172
<211> LENGTH: 40
<212> TYPE: RNA
<213> ORGANISM: Artificial Sequence
<220> FEATURE:
<223> OTHER INFORMATION: Aptamer

<400> SEQUENCE: 172
acacugcgug cuuacgacuu cuggucccau cauucggcua                                40

<210> SEQ ID NO 173
<211> LENGTH: 40
<212> TYPE: RNA
<213> ORGANISM: Artificial Sequence
<220> FEATURE:
<223> OTHER INFORMATION: Aptamer

<400> SEQUENCE: 173
aguucgauga gggugacacc gccaggagug uuugcuagac                                40

<210> SEQ ID NO 174
<211> LENGTH: 40
<212> TYPE: RNA
<213> ORGANISM: Artificial Sequence
<220> FEATURE:
<223> OTHER INFORMATION: Aptamer

<400> SEQUENCE: 174
acccgucgau aaugacugaa cuuccucuau cuuaaagggg                                40

<210> SEQ ID NO 175
<211> LENGTH: 40
<212> TYPE: RNA
<213> ORGANISM: Artificial Sequence
<220> FEATURE:
<223> OTHER INFORMATION: Aptamer

<400> SEQUENCE: 175
ggguaagggg auguuucugg gauucaagcg ccugauucug                                40

<210> SEQ ID NO 176
<211> LENGTH: 40
<212> TYPE: RNA
<213> ORGANISM: Artificial Sequence
<220> FEATURE:
<223> OTHER INFORMATION: Aptamer

<400> SEQUENCE: 176
ucuguauuug uacgcaccga agauaagaga gggaguggau                                40

<210> SEQ ID NO 177
<211> LENGTH: 40
<212> TYPE: RNA
<213> ORGANISM: Artificial Sequence
<220> FEATURE:
<223> OTHER INFORMATION: Aptamer

<400> SEQUENCE: 177
caugggcggg ccgcggucua uucgggauua uugcggaucc                                40

<210> SEQ ID NO 178
```

```
<211> LENGTH: 40
<212> TYPE: RNA
<213> ORGANISM: Artificial Sequence
<220> FEATURE:
<223> OTHER INFORMATION: Aptamer

<400> SEQUENCE: 178
ucagggugug aaguucuucc gcgcuagugg cuuguauguu                              40

<210> SEQ ID NO 179
<211> LENGTH: 40
<212> TYPE: RNA
<213> ORGANISM: Artificial Sequence
<220> FEATURE:
<223> OTHER INFORMATION: Aptamer

<400> SEQUENCE: 179 gucggguug caaggcgucg uagcguguau uugugauggu                               40

<210> SEQ ID NO 180
<211> LENGTH: 40
<212> TYPE: RNA
<213> ORGANISM: Artificial Sequence
<220> FEATURE:
<223> OTHER INFORMATION: Aptamer

<400> SEQUENCE: 180
gcguaugggc gggucauuag gacaauuuaa ccacucgcga                              40

<210> SEQ ID NO 181
<211> LENGTH: 40
<212> TYPE: RNA
<213> ORGANISM: Artificial Sequence
<220> FEATURE:
<223> OTHER INFORMATION: Aptamer

<400> SEQUENCE: 181
auugucugug ugacuagucg gucuagugug ggggagaaga                              40

<210> SEQ ID NO 182
<211> LENGTH: 40
<212> TYPE: RNA
<213> ORGANISM: Artificial Sequence
<220> FEATURE:
<223> OTHER INFORMATION: Aptamer

<400> SEQUENCE: 182
uuaccacuga guuaauuugu acggcugcg guguacuuua                               40

<210> SEQ ID NO 183
<211> LENGTH: 40
<212> TYPE: RNA
<213> ORGANISM: Artificial Sequence
<220> FEATURE:
<223> OTHER INFORMATION: Aptamer

<400> SEQUENCE: 183
gcuaucaaua uuauagaggc ggucggggua gugucaucgu                              40

<210> SEQ ID NO 184
<211> LENGTH: 40
<212> TYPE: RNA
<213> ORGANISM: Artificial Sequence
<220> FEATURE:
<223> OTHER INFORMATION: Aptamer

<400> SEQUENCE: 184
```

```
uaggagagcg ggagcugaga acuuagaggc gccgauacac                                40

<210> SEQ ID NO 185
<211> LENGTH: 40
<212> TYPE: RNA
<213> ORGANISM: Artificial Sequence
<220> FEATURE:
<223> OTHER INFORMATION: Aptamer

<400> SEQUENCE: 185
gacguauuac aguuaaguug gcgccauucg auuucugauc                                40

<210> SEQ ID NO 186
<211> LENGTH: 40
<212> TYPE: RNA
<213> ORGANISM: Artificial Sequence
<220> FEATURE:
<223> OTHER INFORMATION: Aptamer

<400> SEQUENCE: 186
auaccagcuu auucaauuau accagcuuau ucaauuugu                                 40

<210> SEQ ID NO 187
<211> LENGTH: 40
<212> TYPE: RNA
<213> ORGANISM: Artificial Sequence
<220> FEATURE:
<223> OTHER INFORMATION: Aptamer

<400> SEQUENCE: 187
ccguaagucc ggucuuccuu gcugagucgc ccuuucaggu                                40

<210> SEQ ID NO 188
<211> LENGTH: 40
<212> TYPE: RNA
<213> ORGANISM: Artificial Sequence
<220> FEATURE:
<223> OTHER INFORMATION: Aptamer

<400> SEQUENCE: 188
uuggugggga gggccaguua ggucuaauuu ccgacgcgca                                40
```

METHOD AND APPARATUS FOR ANALYZING BIOMOLECULES BY USING OLIGONUCLEOTIDE

CROSS-REFERENCE TO RELATED APPLICATIONS

This application is a national phase application of PCT Application No. PCT/KR2014/009870, filed on Oct. 21, 2014, which claims the benefit and priority of Korean Patent Application No. 10-2013-0143495, filed Nov. 25, 2013 and Korean Patent Application No. 10-2013-0125087, filed Oct. 21, 2013. The entire disclosures of the applications identified in this paragraph are incorporated herein by reference.

FIELD

The present disclosure relates to a method for the analysis of biomolecules. More particularly, the present disclosure relates to a method and an apparatus for analyzing biomolecules in a biological sample using an analysis ligand binding to various target molecules and an oligonucleotide perfectly complementary to a specific region of a target nucleic acid, whereby the biological significance of biomolecules can be analyzed in a single examination.

BACKGROUND

A biomolecule or biological molecule is any molecule that is present in living organisms, including proteins, carbohydrates, lipids, and nucleic acids. With advances in physics, biochemistry and bioinformatics, techniques for analyzing biomolecules and producing comprehensive information on quantitative states, that is, profiles, of biomolecules in biological samples have been developed. However, there is still a need for a novel, efficient method and apparatus due to problems with conventional methods and apparatuses, including difficulty of use, maintenance costs, feasibility, accuracy, sensitivity, testing time and process automation ability.

Techniques for producing a profile of a biomolecule in a biological sample, although not the ultimate object but a means to approach the object, find a wide range of application in various fields including medicine, veterinary science, environmental engineering, food engineering, the agriculture industry and the like.

Profiles of biomolecules including nucleic acid, proteins and other organic substances as constituents of tissues, cell mass, microorganisms, etc. are constructed by means of various methods using physical and chemical properties.

A clinical decision support system is a health information technology system that is designed to analyze the biological significance of biomolecules in biological samples using the profiles, with the aim of performing decision making tasks for physicians and other health professionals for diagnosis and treatment. Clinical decision support systems are largely classified as Case-Based Machine Learning Inference Systems and Expert Systems. In the Case-Based Machine Learning Inference Systems, the clinical information and biological information of known disease-carrying patients, that is, the profiles of biomolecules of patients, are collected, and a disease of interest is inferred or determined from the given clinical and biological information using machine learning on the basis of the collected data. The Expert System is a computer system that is designed to diagnose a disease using rules set forth by medical experts.

With regard to nucleic acids and proteins representative of biomolecules, genetic information is stored in a deoxyribonucleic acid (DNA), which is organized into long structures called chromosomes. About 3 billion nucleotides are included in the human genome. The nucleotide sequences in each chromosome play a critical role in forming the characteristics of individual subjects. Many diseases are based on modifications of the nucleotide sequences in the human genome. Gene codes in genomes belonging to individuals of the same species may differ from one biological individual to another, exhibiting variation in nucleotide sequence, called polymorphism. Causes of polymorphism include the deletion and/or insertion of at least one nucleotide, and the repetition of a certain base sequence. Single nucleotide polymorphism (SNP) is a variation in a single nucleotide that occurs at a specific position in the genome.

Genotypic chemistry analysis methods for many SNPs include PCR-restriction fragment length polymorphism analysis, single-strand conformation polymorphism detection, dideoxy minisequencing, oligonucleotide ligation assays, allele-specific polymerase chain reaction (hereinafter referred to as "AS PCR") analysis, ligase chain reaction analysis, primer-required nucleotide incorporation assays, and fluorescence energy transfer-based assays (Landegren, U., et al., 1998, Genome Res, 8:769-776; Gut, I. G., 2001, Hum Mutat, 17:475-492; Shi, M. M., 2001, Clin. Chem., 47:164-172). In addition, mass spectrometry (Ross P et al., 2000, BioTechniques, 29:620-629) and oligonucleotide microarray-based analysis (Wang, D. G. et al., 1998, Science, 280:1077-1082) have recently been suggested for direct determination of the mass of short single DNA fragments with accuracy.

Allele-specific hybridization was developed for Affymetrix whole genome SNP array (Komura D., et al., 2006, Genome Res. 2006; 16: 1575-84. 6), Idaho Hi-Res Melting curve analysis system (Graham R., et al., 2005, Clin. Chem. 51: 1295-8), dynamic allele-specific hybridization (DASH) (Prince J. A., et al., 2001, Genome Res. 11: 152-62), and Illumina Golden Gate SNP Genotyping Arrays (Gunderson K. L., et al., 2005, Nat Genet. 37: 549-54), and fluorescence resonance energy transfer (FRET) is used in TaqMan (Holloway J. W., et al., 1999, Hum Mutat. 14: 340-7). Molecular beacon assays were developed and described in Barreiro L. B., et al., 2009, Methods Mol Biol. 578: 255-76. Extension techniques used AS PCR are found in Illumina Infinium bead array (Oliphant A., et al., 2002, Biotechniques. Suppl: 56-8, 60-1), Beckman GenomeLab SNPstream system (Bell P. A., et al., 2002, Biotechniques. 2002; Suppl: 70-2, 74, 76-7), and Sequenom MassARRAY SNP system (Hayes B. J., et al. 2007, Bioinformatics. 2007; 23: 1692-3).

Since such techniques for identifying SNP exhibit relative advantages and disadvantages depending on the purpose, it cannot be said that one technique is better than another. However, a DNA-based microarray technique has attracted great attention because it can simply analyze the existence, quantity or expression pattern of specific genes or gene clusters (Schena et al., 1995, Science, 270:467-470; DeRisi et al., 1996, Nature Genetics 14:457-460).

In each cell, about 50,000-100,000 genes exist, but are selectively used. A significant number of the genes are required for the maintenance of basic cellular functions. These genes are called housekeeping genes (hereinafter referred to as "HKG"). In addition, an endogenous standard expression gene is used as a control in revealing the function of a certain gene, searching for a gene having a specific function, or examining the expression pattern of a gene under given conditions. According to various molecular biological purposes, the quantitative analysis of messenger RNA (hereinafter referred to as "mRNA") is used to compare expression levels of certain or multiple genes, as implemented by many techniques including reverse transcriptase polymerase chain reaction (hereinafter referred to as "RT-PCR"), quantitative real time PCR (hereinafter referred to as "qRT-PCR"), serial analysis of gene expression (hereinafter referred to as "SAGE") or microarray assay.

However, conventional DNA microarrays, which are designed to detect target sequences only through hybridization, are still plagued by the problem of false positives due to cross reaction, and thus require improvement in the reliability of the hybridization signal. In addition, conventional microarrays require very strict post-hybridization washing steps and indispensably require the denaturation of a target sequence into a single strand prior to hybridization. On-chip PCR has recently been developed as a heterogeneous assay system, like conventional microarrays, to detect target genes through hybridization or probe extension, but suffers from the disadvantages of impossibility of real-time detection and difficulty of accurate quantitation.

In addition, protein chips or aptamer chips have been developed on the basis of high-throughput screening techniques to track the interactions and activities of proteins, and to determine their functions (Smith et al., Mol Cell Proteomics, 11-18. 2003; and McCauley et al., Anal Biochem, 319(2), 244-250. 2003). The chip consists of a support surface, such as a glass slide, nitrocellulose membrane, bead or microtiter plate, to which an array of capture proteins is bound.

Further, biomolecules are identified by profiling, isolated, and analyzed for their constitution by MALDI-TOF (Matrix Assisted Laser Desorption/Ionization-Time Of Flight). In recent years, protein profiles have been under extensive study using SELDI-TOFMS (Surface-Enhanced Laser Desorption/Ionization Time Of Flight Mass Spectrometry) (Adam et al., Cancer Research, 62, 3609-3614. 2002; Li et al., Clinical Chemistry, 48, 1296-1304. 2002; and Petricoin et al., The Lancet, 359, 572-577. 2002). As a further approach, immuno-PCR (IPCR), in which signals are amplified using a DNA and polymerase (Sano et al., Science 258, 120-122. 1992), has been suggested.

As described above, there have been many developments in such assays in terms of detection sensitivity and multiple analytical potential, but they are in need of the reduction of cost and time, and the improvement of sensitivity and reproducibility.

The present inventor suggested a reverse-SELEX method for producing profiles of proteins (Korean Patent No. 10-0670799), an aptamer-based nucleic acid chip (Korean Patent No. 10-0464225), a method for analyzing biological significance using an aptamer-based nucleic acid chip (Korean Patent No. 10-0923048), and a method for analyzing genetic variation (Korean Patent Application No. 10-2013-0118222호), but they are unable to analyze both proteins and nucleic acids simultaneously in biological samples, which can be achieved in the present disclosure.

The comprehensive analysis of biomolecules in biological samples allows for the production of profiles of biomolecules associated with diseases.

Comprehensive research into biomolecules of biological samples may be characterized by analyzing profiles of biomolecules associated with diseases, thereby identifying biomolecules that allows for the diagnosis of diseases or the analysis of therapeutic effects, biomolecules playing an important role in the onset and progression of diseases, biomolecules responsible for susceptibility to diseases, and target molecules for the development of novel drugs.

Leading to the present invention, intensive and thorough research into the analysis of biomolecules, conducted to overcome the problems encountered in the conventional techniques for analyzing biomolecules separately, resulted in the development of a method for analyzing all of the biomolecules responsible for a given biological event at once, in real time with improved efficiency and sensitivity.

Ultimately, the holistic analysis of biomolecules in a biosample with the production of biological profiles thereof can be applied to the diagnosis of diseases, the analysis of therapeutic effects, and the identification of biomolecular principles that play an important role in the onset and progression of disease or which are responsible for susceptibility to disease, and target molecules for the development of novel drugs.

DISCLOSURE

Technical Problem

In order to accomplish the above object, the present disclosure provides a method and an apparatus for analyzing two or more different biomolecules, using an oligonucleotide, the method and the apparatus comprising analyzing the two or more different biomolecules at the nucleic acid level, the two or more different biomolecules including at least one protein molecule and being isolated from a sample to be analyzed.

Also, the present disclosure provides a method and an apparatus for analyzing a biomolecule, using an oligonucleotide, comprising preparing a receptor and a nucleic acid from the biomolecule of a sample; reacting the receptor with an analysis ligand to form a receptor-analysis ligand complex; preparing a target DNA from a target nucleic acid to be analyzed and a target nucleic acid as an oligonucleotide of the receptor-analysis ligand complex; and analyzing the target DNA, whereby the biological significance of the receptor for an aptamer and of the nucleic acid is identified, whereby the biological significance of the biomolecule can be determined in the biological sample.

In addition, the present disclosure provides a nucleic acid chip capable of analyzing biomolecules in a biological sample in a single assay, whereby the biological significance of the biomolecule can be determined in the biological sample.

In some embodiments, the biological sample is at least one selected from the group consisting of cells, fungi, viruses, cell lines, and tissues.

The object of the present disclosure is to provide a method and an apparatus for analyzing a biomolecule, using an oligonucleotide, whereby various biological significances including diseases associated with the biomolecules can be analyzed from the information effectively produced as a result of binding patterns of oligonucleotides.

Technical Solution

As used herein, the term "biomolecule" means a special molecule that exhibits a biological function as a constituent of an organism, as exemplified by macromolecules such as proteins, nucleic acids, polysaccharides, and lipids, small molecules such as amino acids, nucleotides, monosaccharides, vitamins, metals such as iron, copper, and the like, inorganic substances, etc.

As used herein, the term "ligand" refers to a biomolecule that binds to a receptor. Representative among the scope of ligands are an antibody, a peptide, a nucleic acid, and an aptamer. The term "receptor" is intended to encompass almost all chemical or biological effectors as target molecules, irrespective of their size. Examples of the receptor include a protein, a peptide, a nucleic acid, a carbohydrate, a lipid, a polysaccharide, a glycoprotein, a hormone, a receptor, an antigen, an antibody, a virus, a pathogen, a toxic material, a substrate, a metabolite, a transition state analog, a cofactor, an inhibitor, a drug, a dye, a nutrient, a growth factor, a cell, and a tissue, but are not limited thereto.

In the present disclosure, a receptor refers to a molecule or molecular cluster that is specific for one or more ligands. When bound or associated with ligand(s), a receptor undergoes a conformational change to thus trigger a physiological response, such as in an agonist or antagonist.

An antibody is a protein that binds to an antigen to form an antigen-antibody complex that exhibits an immunological function in response to the invasion of the antigen. An aptamer is a small single-stranded nucleic acid (DNA or RNA) fragment (20-60 nucleotides long) that can bind to a variety of receptors ranging from low molecular weight compounds to proteins, with high affinity and specificity.

As used herein, the term "analysis ligand" refers to a structure in which a specific ligand is conjugated with an oligonucleotide. The oligonucleotide may be adapted for analyzing a biomolecule that serves as a receptor to which a ligand binds. The oligonucleotide of the analysis ligand has the structure represented by the following Formula I:

$$5'\text{-}P1\alpha\text{-}T\text{-}P3\beta\text{-}3' \tag{I}$$

wherein,

P1 is a region complementary to a forward primer of a pair of signal primers,

T is a region, complementary to a capture probe, which is designed to serve as a probe in a hybridization reaction, discriminating a target protein or a nucleic acid representing single stranded nucleic acid, P3 is a region complementary to a backward primer of the pair of primers carrying the detection signal, and α and β are each an integer of 8-30, representing the number of nucleotides in the corresponding regions.

The term "target nucleic acid", as used herein, means a nucleic acid isolated from a sample to be analyzed. It may be in the form of a polynucleotide that has nucleotide sequences complementary to at least part of an upstream oligonucleotide and at least part of a downstream oligonucleotide, respectively. In some embodiments, the target nucleic acid may have an extension region or a nick between the two regions respectively complementary to the upstream and the downstream oligonucleotide. The target nucleic acid may include single- or double-stranded DNA or RNA. In addition, a target DNA refers to a template DNA to which the upstream oligonucleotide and the downstream oligonucleotide bind directly.

To accomplish the above objects, the present disclosure provides a method and an apparatus for analyzing two or more different biomolecules, comprising analyzing the two or more different biomolecules at the nucleic acid level, the two or more different biomolecules including at least one protein molecule and being isolated from a sample to be analyzed.

In a biological sample, there are numerous biomolecules that can be associated with ligands. In this regard, biomolecules form biomolecule-ligand complexes, so that they can be detected by means of a ligand signal. Based on this detection, techniques of analyzing biomolecules have been developed.

The present disclosure provides a method and an apparatus for analyzing a biomolecule, using an oligonucleotide, the method and the apparatus comprising: preparing a receptor and a nucleic acid from the biomolecule of a sample; reacting the receptor with an analysis ligand to form a receptor-analysis ligand complex; preparing a target DNA from a target nucleic acid to be analyzed and a target nucleic acid as an oligonucleotide of the receptor-analysis ligand complex; and analyzing the target DNA, whereby the biological significance of the receptor for an aptamer and of the nucleic acid is identified.

FIG. 1 is an overall flow diagram illustrating the determination of biological significance of a biomolecule in a biological sample by isolating nucleic acids and proteins separately, reacting the proteins with an analysis ligand to form a protein-analysis ligand complex, separating the nucleic acids into RNA and DNA, preparing a target DNA covering a target nucleic acid to be analyzed, and analyzing the target DNA with an oligonucleotide perfectly complementary to a specific region of the target nucleic acid.

FIG. 2 is a schematic view of a complex between a receptor isolated from a biological sample and an analysis ligand that comprises a ligand and an oligonucleotide composed of a nucleotide sequence representing the ligand, and universal PCR primers.

In a particular embodiment of the present disclosure, a biological sample, particularly cells, is lysed, and biomolecules serving as receptors are extracted from the lysate, and subsequently nucleic acids such as DNA and RNA are isolated from the remnant, using a method known in the art. The biomolecule thus obtained is reacted with an aptamer to form a biomolecule-analysis ligand complex which is then isolated using one of various known methods. Preferably, the isolation of the biomolecule-analysis ligand complex may be achieved by immobilizing the biomolecule onto a support, reacting an analysis ligand with the immobilized biomolecule to form a biomolecule-analysis ligand complex, and washing the support to remove) unbound analysis ligands. The RNA, DNA and biomolecule-analysis ligand complex isolates may be used as target nucleic acids to be analyzed and may be subjected to quantitative analysis and mutation analysis. From the analysis results thus obtained, the biological significance of the biomolecule in the biological sample can be determined.

In another embodiment of the present disclosure, the method and the apparatus for analyzing a biomolecule are characterized in that a specific nucleic acid is analyzed for quantity, mutation or methylation.

The specific nucleic acid mutation may be a genetic variant exemplified by single nucleotide polymorphism (SNP) and structural variation. Genetic variants are known to induce differences among individuals in phenotype, susceptibility to disease, and response to therapeutic drugs. Particularly, mutations involved in the onset and progression of disease are called Disease-associated Genetic Variants. SNP refers to genetic variation or mutation in a single nucleotide (A, T, G, C) that occurs at a specific position in the genome. Structural variation is the variation in structure of an organism's chromosome. It consists of many kinds of variation in the genome of one species, and usually includes microscopic and submicroscopic types, such as deletions, duplications, copy-number variants, insertions, inversions and translocations.

In addition, the analysis for nucleic acid methylation may be implemented by treating a nucleic acid with bisulfite. Upon treatment with bisulfite, unmethylated cytosine residues are converted into uracil residues while methylated cytosine residues remain unchanged. The change of nucleotides before and after treatment with bisulfite indicates the methylation of nucleic acids.

In another embodiment of the present disclosure, internal quality control for the quantitative analysis of the aptamer receptor employs a material that is not found in the biological sample to be analyzed.

As for qualitative and quantitative analysis, quality control is generally conducted with biomolecules included in a biological sample to be analyzed for comparison in various tests and examinations. For use in quality control, a material that is present at a relatively constant level in a biological sample to be analyzed is ideal. However, if that condition is impossible to satisfy, a heterogeneous substance that is not found in the sample may be employed. Particularly, a heterogeneous biomolecule that is not included in a biosample to be analyzed may be used as a substance for quality control. Quality control means internal quality control designed to manage the precision of measurements by analyzing a group of test data obtainable in each round, without employing an external reference such as a control sample.

When a biological sample of human origin is analyzed, a material for internal quality control may be preferably a plant-specific biomolecule that is not found in the biological sample of human origin. At present, the human genome project and the *Arabidopsis thaliana* genome project have been completed, and plant-specific proteins have been reported. In the present disclosure, a plant-specific protein may be used as a reference material for the analysis of a biological sample of human origin.

In a particular embodiment of the method and apparatus for analyzing a biomolecule, the target nucleic acid is quantitatively analyzed, or is subjected to base sequencing.

The analysis of the nucleic acid may be performed by PCR (polymerase chain reaction), LCR (ligase chain reaction), SDA (strand displacement amplification), TMA (transcription-mediated amplification), bDNA (branched DNA), an invader method, and/or RCA (rolling circle amplification). Particularly, a double-stranded nucleic acid obtained from the nucleic acid via LCR is used as a template for PCR amplification and the PCR product is analyzed.

In accordance with another embodiment of the method and apparatus for analyzing a biomolecule using an oligonucleotide, the step of preparing a target DNA from a target nucleic acid to be analyzed and a target nucleic acid as an oligonucleotide of the receptor-analysis ligand complex comprises preparing an upstream oligonucleotide and a downstream oligonucleotide, both perfectly complementary to the target nucleic acid in the same direction; reacting the upstream oligonucleotide and the downstream oligonucleotide with the target nucleic acid to form a complete double-stranded nucleic acid; producing a target probe by amplification in the presence of a set of signal primers, with the complete double-stranded nucleic acid serving as a template; and hybridizing the target probe with a capture probe and analyzing a signal produced from the hybrid.

The term "nucleotide sequence complementary to" the target nucleic acid, as used herein, refers to a nucleotide sequence sufficiently long to allow for the hybridization of oligonucleotides. Its length ranges from about 6 to about 1,000 nucleotides, preferably from about 8 to 30 nucleotides, and optimally from 10 to 25 nucleotides.

As used herein, the terms "upstream oligonucleotide" and "downstream oligonucleotide" refer to oligonucleotides that are perfectly complementary to the target nucleic acid at an upstream site and a downstream site, respectively.

In accordance with the present disclosure, the upstream oligonucleotide is a nucleotide sequence that is particularly 6 to 100 bases long, more particularly 8 to 30 bases long, and most particularly 20 bases long.

In accordance with the present disclosure, the downstream oligonucleotide is a nucleotide sequence particularly 8 to 80 bases long and most particularly 10 to 20 bases long, having a 3' region at least partially complementary to the target nucleic acid.

The term "capture probe", as used herein, refers to a distinct nucleotide sequence useful for identifying a polynucleotide and/or tracing the source of the polynucleotide. A capture probe sequence may be present at the 5'- or 3'-terminus of the signal primer. The capture probe nucleotide sequence may vary extensively in size and composition. With regard to instruction for the selection of a series of capture probe nucleotide sequences suitable for use in the present disclosure, reference may be made to the following documents (U.S. Pat. No. 5,635,400; Brenner et al, 2000, PNAS., 97: 1665-1670; Shoemaker et al, 1996, Nature Genetics, 14: 450-456; EU Patent No. 0799897A1; U.S. Pat. No. 5,981,179) and the like. In a particular embodiment, the capture probe may range in length from 4 to 36 nucleotides, more particularly from 6 to 30 nucleotides, or most particularly from 8 to 20 nucleotides.

In the present disclosure, the capture probe may have a specific nucleotide sequence of the target nucleic acid.

In accordance with another embodiment of the method and apparatus for analyzing a biomolecule using an oligonucleotide, the upstream oligonucleotide for the quantitative analysis of the target nucleic acid is composed of a region perfectly complementary to a forward signal primer and a region perfectly complementary to the nucleic acid, and the downstream oligonucleotide is composed of a region perfectly complementary to the target nucleic acid and a region perfectly complementary to a backward signal primer.

FIG. 3 is a view illustrating the formation of a double-stranded nucleic acid between a nucleic acid reversely transcribed from an RNA isolate from a biological sample and a set of the upstream oligonucleotide and the downstream oligonucleotide, followed by quantitative analysis.

In another embodiment, the upstream oligonucleotide for the quantitative analysis of the target nucleic acid is composed of (i) a region perfectly complementary to the forward signal primer of a pair of signal primers and (ii) a hybridization region substantially complementary to the target nucleic acid to be hydrolyzed.

In this regard, the upstream oligonucleotide is represented by the following formula II:

$$5'\text{-}P1\alpha\text{-}H\beta\text{-}3' \qquad (II)$$

wherein,

P1 is a region perfectly complementary to the forward primer of a pair of signal primers, H is a hybridization region substantially complementary to a target nucleic acid to be hybridized, and α and β are each an integer of 8 to 30, representing numbers of nucleotides.

As the upstream oligonucleotide, a nucleotide sequence that is perfectly complementary to a certain nucleic acid is useful. However, a nucleotide sequence that is substantially complementary to a certain nucleic acid may be available as the upstream oligonucleotide unless its hybridization is interrupted. Preferably, the upstream oligonucleotide contains a sequence hybridizable to a sequence consisting of 10-30 consecutive nucleotide residues of the certain target nucleic acid.

The downstream oligonucleotide is composed of (i) a region perfectly complementary to the target nucleic acid in the same direction as the upstream oligonucleotide, (ii) a region perfectly complementary to the capture probe, and (iii) a region perfectly complementary to the backward primer of a pair of signal primers.

In this context, the downstream oligonucleotide is represented by the following formula III:

$$5'\text{-H}\alpha\text{-T}\beta\text{-P3}\gamma\text{-}3' \qquad (III)$$

wherein,

H is a region complementary to the target nucleic acid at a site downstream of the 3' end of the upstream oligonucleotide, T is a region, perfectly complementary to a capture probe, which is designed to serve as a probe in a hybridization reaction, discriminating a target nucleic acid or a single-stranded nucleic acid representing a target nucleic acid, and P3 is a region complementary to a backward primer of the pair of signal primers, and α, β and γ are each an integer of 8-30, representing numbers of nucleotides in corresponding regions.

In accordance with another embodiment of the method and apparatus for analyzing a biomolecule using an oligonucleotide, an upstream oligonucleotide and a downstream oligonucleotide are constructed for use in analyzing the mutation of a target nucleic acid in the present disclosure. In this regard, the upstream oligonucleotide is composed of a region perfectly complementary to the forward signal primer, a nucleotide sequence perfectly complementary to the target nucleic acid, and a 3' terminal region capable of discriminating the mutated nucleotides of the target nucleic acid, and the downstream oligonucleotide is composed of a region perfectly complementary to the nucleic acid, a region perfectly complementary to the capture probe, and a region perfectly complementary to the backward signal primer.

FIG. 4 is a view illustrating the isolation of nucleic acids and receptors from a biological sample and the formation of a target nucleic acid from the nucleic acids and the receptor-analysis ligand complex prepared from the isolates, followed by analyzing the mutation of a target nucleic acid with oligonucleotides perfectly complementary to certain regions of the nucleic acid.

FIG. 5 is a view illustrating the preparation of a target DNA by treating a nucleic acid isolate from a biological sample with bisulfite, followed by analyzing the methylation of the target DNA with oligonucleotides perfectly complementary to certain regions of the target DNA.

Also, an upstream oligonucleotide and a downstream oligonucleotide are constructed for use in analyzing the mutation of a target nucleic acid. In this regard, the upstream oligonucleotide may be composed of (i) a region perfectly complementary to a forward primer of a pair of signal primers (P1), (ii) a variation-adjacent region perfectly hybridizable to a target nucleic acid, and (iii) a variation region covering a mutant nucleotide. The upstream oligonucleotide carrying information on nucleotide variation may consist of two or more different oligonucleotides.

In this context, the upstream oligonucleotide is represented by the following formula (IV):

$$5'\text{-P1}\alpha\text{-H}\beta\text{-V}\gamma\text{-}3' \qquad (IV)$$

wherein,

P1 is a region perfectly complementary to a forward primer of a pair of signal primers, H is a variation-adjacent region having a hybridization sequence perfectly complementary to a target nucleic acid, V is a variation-specific region covering the variation of the target nucleic acid, and α, β, and γ represent numbers of nucleotides in corresponding regions, α and β each being an integer of 8-30 and γ being an integer of 1-3.

As the upstream oligonucleotide, a nucleotide sequence that is perfectly complementary to an SNP-carrying nucleic acid is useful. However, a nucleotide sequence that is substantially complementary to the SNP-carrying nucleic acid may be available as the upstream oligonucleotide unless its hybridization is interrupted. Preferably, the upstream oligonucleotide contains a sequence hybridizable to a sequence consisting of 10-30 consecutive nucleotide residues of the SNP-carrying target nucleic acid. More preferably, the upstream oligonucleotide has a nucleotide complementary to the SNP nucleotide at its 3' end. As a rule, the stability of a duplex formed by hybridization tends to be dependent on the sequence matching of terminal sites. Hence, if the upstream oligonucleotide carrying a 3' terminal nucleotide complementary to an SNP nucleotide fails to hybridize at the terminal region, the duplex is apt to dissociation in stringent conditions.

The downstream oligonucleotide is composed of (i) a region perfectly complementary to the target nucleic acid in the same direction as the upstream oligonucleotide (H), (ii) a region perfectly complementary to the capture probe (T), and (iii) a region perfectly complementary to a backward primer of a pair of signal primers (P3).

In this regard, the downstream oligonucleotide is represented by the following formula V:

$$5'\text{-H}\alpha\text{-T}\beta\text{-P3}\gamma\text{-}3' \qquad (V)$$

wherein,

H is a variation-adjacent region perfectly complementary to the target nucleic acid, T is a region, perfectly complementary to a capture probe, which is designed to serve as a probe in a hybridization reaction, discriminating a mutation-carrying, single-stranded nucleic acid representing a target nucleic acid, P3 is a region complementary to a backward primer of the pair of signal primers, and α, β and γ are each an integer of 8-30, representing numbers of nucleotides in corresponding regions.

The upstream oligonucleotide and the downstream oligonucleotide can be synthesized and prepared using a method known in the art (such as chemical synthesis). Alternatively, the upstream oligonucleotide and the downstream oligonucleotide can be conveniently obtained from a commercial supplier.

The upstream oligonucleotide and the downstream oligonucleotide useful in the present disclosure are hybridized or annealed with a template at predetermined regions to form a duplex. With regard to a nucleic acid hybridization condition suitable for the formation of such a duplex, reference may be made to Joseph Sambrook, etc., Molecular Cloning, A Laboratory Manual, Cold Spring Harbor Laboratory Press, Cold Spring Harbor, N.Y. (2001); and Haymes, B. D., etc., Nucleic Acid Hybridization, A Practical Approach, IRL Press, Washington, D.C. (1985).

In the present disclosure, the annealing is carried out in a stringent condition that allows the signal primers to bind specifically to a target nucleotide sequence. The stringent condition for annealing is sequence-dependent and may vary depending on environmental variables. The target nucleic acid thus amplified carries multiple target sites on one molecule so that it can be used in the simultaneous analysis of multiple target positions.

In the method and apparatus for analyzing a biomolecule using an oligonucleotide according to the present disclosure, when an extension region exists between the respective partial duplexes formed through the hybridization of the target nucleic acid to the upstream and the downstream oligonucleotide, extension is carried out, followed by ligation to produce a complete duplex.

As used herein, the term "extension region" refers to a nucleotide sequence long enough to allow for the extension of an oligonucleotide through nucleic acid polymerization. The "extension region" may be present in some embodiments of the target or template nucleic acids. If existing, the "extension region" is located between the upstream oligonucleotide and the downstream oligonucleotide, both of which are bound to the target or template nucleic acid. The "extension region" may range in length from about 1 to 1,000 nucleotides, preferably from about 1 to 100 nucleotides, more preferably from 3 to 50 nucleotides, and optimally from 3 to 10 nucleotides.

The term "extension", as used herein, is intended to mean the prolongation of a primer bound to the target nucleic acid so as to fill the extension region. The oligonucleotide completely bound to the nucleic acid is extended, with the nucleic acid serving as a template. In the present disclosure, the extension may be achieved using a DNA polymerase. It may be selected from the group consisting of Taq DNA polymerase and Pfu DNA polymerase. However, so long as it is thermostable, any DNA polymerase may be employed.

The term "ligation", as used herein, is intended to mean the enzymatic connection of the 3' end of the upstream oligonucleotide, whether extended or not, to the downstream oligonucleotide. The ligation may be carried out using a ligase. In the present disclosure, the ligase may be selected from among $E.\ coli$ DNA ligase, Tag DNA ligase, T4 DNA ligase, and Ampligase ligase.

In the method and apparatus for analyzing a biomolecule using an oligonucleotide according to the present disclosure, when a nick exists between the respective partial duplexes formed through the hybridization of the target nucleic acid to the upstream and the downstream oligonucleotide, ligation is carried out to produce a complete duplex.

As described above, the ligation is the inter-nucleotide connection catalyzed by a ligase. When two different oligonucleotides with respective lengths are complementarily bound in series to adjacent sites of a target nucleic acid, a nick is formed between the two partial duplexes thus formed. The nick can be sealed using DNA ligase to thus connect the two separate oligonucleotides into a single strand. Hence, any ligase that is known to close nicks in the phosphodiester backbone of DNA can be employed in the present disclosure without limitations.

Examples of the ligase available for the present disclosure include $E.\ coli$ DNA ligase, Taq DNA ligase, T4 DNA ligase, and Ampligase ligase, but are not limited thereto. Any enzyme with DNA ligation activity may be used.

In addition, even when two or more different oligonucleotides are used, ligation can be achieved in a single reaction. To this end, the individual oligonucleotides to be ligated are selected such that melting temperatures (Tm) of their sequences, hybridized to a target nucleic acid, may differ by 5° C. or less.

In the method and apparatus for analyzing a biomolecule using an oligonucleotide according to the present disclosure, the production of the complete duplex by hybridizing the upstream oligonucleotide and the downstream oligonucleotide with the target nucleic acid and then ligating the partial duplexes to each other is carried out two or more times.

In the method and apparatus for analyzing a biomolecule using an oligonucleotide according to the present disclosure, the signal primers are composed of a universal forward PCR primer carrying a detection marker, and a universal backward PCR primer.

The signal primers are represented by the following formulas VI and VII, respectively:

Forward primer: 5'-X-P-3'   (VI)

Backward primer: 5'-P-3'   (VII)

wherein X is a detectable marker. For use in the quantitative analysis of a biomolecule, a marker used for a target probe from a control sample may be different from that used for a test sample. The marker may be Cy3 for the former and Cy5 for the latter.

Further, a marker may be utilized to analyze the mutation of a nucleic acid. For example, a fluorescent report molecule or a report molecule with a physical property may be linked to the 5' end of a primer for discriminating mutant nucleotides. Preferably, Cy3 may be used as a marker for a primer for wild-type nucleic acids while a primer for mutant nucleic acids may be labeled with Cy5.

In formulas VI and VII, P is a nucleotide sequence perfectly complementary to a region of the upstream oligonucleotide or the downstream oligonucleotide.

Of the signal primer pair, the forward primer (P1 or P2) has a nucleotide sequence perfectly complementary to a region of the upstream oligonucleotide, and may preferably be a universal PCR primer. It may be labeled at the 5' end with a marker (X), such as a fluorescent reporter molecule or a reporter molecule having a particular physical property, which may be selected depending on the nucleotide mutation of the target nucleic acid. After hybridization, the nucleotide mutation can be determined using the signal produced from the marker.

The backward primer (P3) has a nucleotide sequence perfectly complementary to a region of the downstream oligonucleotide, and may preferably be a universal PCR primer. A universal PCR primer refers to an oligonucleotide having a highly conserved nucleotide sequence useful for PCR, and may be available for many commercial cloning vectors.

In the method and apparatus for analyzing a biomolecule using an oligonucleotide according to the present disclosure, the capture probe has a nucleotide sequence perfectly complementary to a marker-labeled single-stranded nucleic acid of the target probe.

In the method and apparatus for analyzing a biomolecule using an oligonucleotide according to the present disclosure, the capture probe has a nucleotide sequence perfectly complementary to a specific nucleotide sequence of the downstream oligonucleotide on the target probe.

The capture probes are designed to bind to the amplicons, playing a role in discriminating the amplicons. The amplicons that are obtained by amplification in the presence of the signal primers with the target nucleic acid serving as a template may be used to construct, on the basis of the primer-binding region (T), a single-stranded nucleic acid complementary to the marker-labeled single-stranded nucleic acid, an oligonucleotide, and PNA (peptide nucleic acid).

In the method and apparatus for analyzing a biomolecule using an oligonucleotide according to the present disclosure, the target probe includes a control target probe prepared from a control sample and an analysis target prepared from a test sample.

In order to perform quantitative analysis with biomolecules isolated from a control sample and a test sample, a control target probe is constructed by performing PCR in the presence of signal primers on a target DNA prepared from the biomolecules of the control sample while an analysis target probe is constructed by performing PCR in the presence of signal primers on the target DNA prepared from the biomolecules of the test sample. A mixture of the control target probe and the analysis target probe is used. The signal primers used for the construction of the control target probe and the analysis target probe may be labeled with different markers. The primers may be labeled with Cy3 for the former and with Cy5 for the latter.

In the method and apparatus for analyzing a biomolecule using an oligonucleotide according to the present disclosure, the capture probe is immobilized onto a support.

In the present disclosure, the support is selected from among a glass slide, a detection surface of a biosensor, a bead, and a nanoparticle.

FIG. 6 is a view illustrating the hybridization of a marker-labeled target probe with the capture probes immobilized onto a glass slide, followed by washing and analyzing generated signals to determine the biomolecule.

Preferably, the capture probes may be fixed to a glass slide or to a detection surface of a biosensor. For this, it may be modified to allow for the fixation. The modification may be the addition of a C1-C20 alkyl group to the 5' end of the oligonucleotide. Alternatively, a thiol group may be added so as to facilitate the fixation. However, the modification may be suitably altered according to the purpose.

The support to which the capture probes are fixed is a kind of microarray, or may be a detection sensor of a biosensor. So long as it detects a change occurring upon the binding of a target material, any support may be employed to sense the target material in the present disclosure. Particularly, fluorescence can be detected from a fluorescent material bound to the capture probe. Herein, a glass slide is preferably employed.

The hybridization may be carried out at an annealing temperature of 40° C. to 70° C., preferably at an annealing temperature of 45° C. to 68° C., more preferably at an annealing temperature of 50° C. to 65° C., and most preferably at an annealing temperature of 60° C. to 65° C. With regard to hybridization conditions, reference may be made to Joseph Sambrook, et al., Molecular Cloning, A Laboratory Manual, Cold Spring Harbor Laboratory Press, Cold Spring Harbor, N.Y. (2001), and Haymes, B. D., et al., Nucleic Acid Hybridization, A Practical Approach, IRL Press, Washington, D.C. (1985). A stringent condition for the hybridization may be determined by many factors including temperature, ion strength (buffer concentration), organic solvents, etc. The stringent condition may vary depending on the sequence to be hybridized. For example, the stringent condition may be a high stringent condition. In this regard, hybridization at 65° C. in a buffer containing 0.5 M $NaHPO_4$, 7% SDS (Sodium Dodecyl Sulfate), and 1 mM EDTA, and washing at 68° C. with 0.1×SSC (standard saline citrate)/0.1% SDS are performed. Alternatively, a high stringent condition may mean washing at 48° C. in 6×SSC/0.05% sodium pyrophosphate. A low stringent condition may mean washing at 42° C. in 0.2×SSC/0.1% SDS.

In the microarray, the capture probes are used as a hybridizable array element immobilized onto a substrate. A preferable substrate may be a suitable solid or semi-solid support, examples of which include a membrane, a filter, a chip, a slide, a wafer, a fiber, a magnetic or non-magnetic bead, a gel, tubing, a plate, a macromolecule, a microparticle, and a capillary tube. The capture probes are arranged and immobilized on the substrate. The immobilization may be achieved by forming covalent bonds, either chemically or under UV light. For example, the capture probes may be bound to an epoxy- or aldehyde-modified glass surface. On a polylysine-coated surface, covalent bonds may be formed under UV. In addition, the hybridizable array element may be bound to the substrate via a linker (e.g., ethylene glycol oligomer and diamine).

An instrument for measuring signals generated from the marker-labeled, single-stranded nucleic acids carrying mutant nucleotides in the amplicons bound to the capture probes is determined depending on the kind of signal. After hybridization, the generated signals are detected. The hybridization signals can be detected using various methods selected depending on the kind of marker that is bound to the capture probes.

Meanwhile, the sample DNA applied to the microarray of the present disclosure may be labeled and hybridized with the capture probes on the microarray. Various hybridization conditions may be used. The detection and analysis of hybridization may be conducted in various manners depending on the marker.

The marker bound to the capture probes provides a signal that allows for determining whether or not hybridization has occurred. The marker may be linked to the oligonucleotide. Examples of the marker useful in the present disclosure include fluorophores (e.g., fluorescein, phycoerythrin, rhodamine, Lissamine, Cy3 and Cy5 (Pharmacia)), chromophores, chemo luminophores, magnetic particles, radioisotopes, ($P^{32}$ and $S^{35}$), mass labels, electron-dense particles, enzymes (alkaline phosphatase, horseradish peroxidase), cofactors, enzyme substrates, heavy metals (e.g. gold), and haptens having specific binding partners, like antibodies, streptavidin, digoxigenin, and other chelating agents, but are not limited thereto. The labeling can be carried out using a typical method, such as a nick translation method, a random priming method (Multiprime DNA labelling systems booklet, "Amersham" (1989)), and a kination method (Maxam & Gilbert, 1989, Methods in Enzymology, 65:499). The marker may generate a signal that can be detected by means of fluorescence, radiation, color development, mass measurement, X-ray diffraction or absorption, magnetism, enzymatic activity, mass analysis, affinity, hybridization, high frequency, or nanocrystals.

The microarray can be fabricated using a suitable method known in the art. Devices useful for the construction of the microarray can be conveniently available from commercial suppliers. Various methods for fabricating nucleic acid chips on which the capture probes are regularly arranged are known in the art (M. Schena, 1999, DNA microarray; a practical approach, Oxford).

In the method and apparatus for analyzing a biomolecule using an oligonucleotide according to the present disclosure, the marker is a fluorescent dye selected from the group consisting of biotin, Cy2, GFP, YO-PRO-1, YOYO-1, Calcein, FITC, FlourX, ALEXA 488, Rhodamine 110, ABI 5-FAM, Oregon Green 500, Oregon green 488, RiboGreen, Rhodamine Green, Rhodamine 123, Magnesium Green, Calcium Green, TO-PRO-1, TOTO-1, ABI JOE, BODIPY 530/550, DiI, BODIPY TMR, BODIPY558/568, BODIPY564/570, Alexa 546, TRITC, Magnesium Orange, Phycoerythrin R & B, Rhodamine Phalloidin, Calcium Orange, Pyronin Y, Rhodamine B, ABI TAMRA, Rhodamine Red, Cy3.5, ABI ROX, Calcium Crimson, Alexa 594, Texas Red, Nile Red, YO-PRO-3, YOYO-3, R-phycocyanin, C-phycocyanin, TO-PRO-3, TOTO-3, DiD DiIC(5), thiadicarbocyanine, Cy5.5, Cy5, and Cy3.

In accordance with another embodiment thereof, the present disclosure provides a method and an apparatus for analyzing a biomolecule, using an oligonucleotide, the method and the apparatus comprising: fabricating a chip on which the capture probes are spotted; hybridizing the target probe with the capture probes immobilized onto the chip and then washing the chip, the target probe being a marker-labeled amplicon; scanning the chip with a laser having a fluorescent dye-specific wavelength; and measuring the fluorescence intensity resulting from the hybridization to analyze the quantity and mutation of the nucleic acid simultaneously.

In accordance with another embodiment thereof, the present disclosure provides a kit for analyzing a receptor and a nucleic acid of a biological sample, using an oligonucleotide, whereby the biological significance of the receptor and the nucleic acid can be determined.

In some embodiments, the apparatus for analyzing a biomolecule using an oligonucleotide is provided for implementing the analysis method. The apparatus comprises a sample treatment unit, in which a receptor and a nucleic acid are prepared from a biological sample, an amplification unit, composed of a module in which the target nucleic acid is prepared and amplified, and a module in which the amplicon is analyzed.

The sample treatment unit and amplification unit in the apparatus of the present disclosure may be composed of a mixing chamber, a lysis chamber, and a reaction chamber, and may be operated in an integrated manner so as to effectively conduct the analysis method.

A sample putatively containing a biomolecule of interest is prepared in a series of preparation steps in the sample treatment unit composed of the mixing chamber and the lysis chamber. The preparation steps may include filtration, cell lysis, the purification of RNA, DNA and receptors, the formation of receptor-analysis ligand complex, and treatment with reagents. In order to guarantee the result of biomolecule analysis, it is useful to avoid contamination during sample preparation. Thus, a method for assaying the validity of a sample prepared for use in nucleic acid amplification is provided.

The sample contains a target entity selected from the group consisting of cells, spores, microorganisms, and viruses. The target entity includes at least one target biomolecule. The method comprises introducing the sample into the unit containing the mixing chamber in which the sample is mixed with a control sample. The control sample is selected from the group consisting of cells, spores, microorganisms, and viruses. The control sample includes a quality control material. The apparatus also comprises a lysis chamber and a reaction chamber. The sample is mixed with a control sample in the mixing chamber.

In another embodiment, the method comprises lysing target entities from a target sample and a control sample to purify a biomolecule, forming a receptor-analysis ligand complex, exposing RNA and DNA, both being isolated in the lysis chamber, as well as the receptor-analysis ligand complex, to nucleic acid amplification conditions, and determining the presence of at least one quality control material. The positive detection of the quality control material indicates that the sample preparation process has been properly conducted. On the other hand, the absence of the quality control material indicates the improper implementation of sample preparation.

Also, the present disclosure provides an amplification apparatus for assaying the validity of a sample prepared for use in nucleic acid amplification. The sample contains a target entity selected from the group consisting of cells, spores, microorganisms, and viruses. The target entity includes at least one target biomolecule. The apparatus comprises a main body including a first chamber for accommodating a control sample to be mixed with the sample. The control sample is selected from the group consisting of cells, spores, microorganisms, and viruses. The control sample includes a quality control material.

The main body also includes a lysis chamber in which target entities from a target sample and a control sample are lysed in order to isolate biomolecules, and the isolates are separated into RNA, DNA, and a receptor. In addition, the main body includes an analysis ligand reacting chamber in which an isolated aptamer receptor is reacted with an aptamer to form a receptor-aptamer complex. Further, the main chamber includes a reaction chamber in which a nucleic acid is maintained for amplification and detection. The apparatus may further comprise at least one fluid controller for inducing a mixture of a sample and a control sample to flow from the first chamber to the lysis chamber, and for inducing the biomolecule, isolated in the lysis chamber, to flow into the reaction chamber.

According to some embodiments, the apparatus may further comprise an ultrasonic transducer, engaged with a wall of the lysis chamber, for proving ultrasonic waves to the wall. In some embodiments, the apparatus may further comprise beads for lysing the sample control and the target entity in the lysis chamber.

Also, contemplated in accordance with another embodiment of the present invention is a method for determining the correct performanceof lysis. This method may further comprise mixing a sample, putatively inferred to contain a target entity selected from the group consisting of cells, spores, microorganisms, and viruses, with a control sample. The target entity includes at least one quality control material. The control sample includes a quality control material. The control sample is mixed with the target entity of the sample and the mixture is lysed. The method may further comprise detecting the quality control material to determine whether or not a biomolecule is isolated from the control sample during the lysis. The positive detection of the quality control material indicates that the sample preparation process was properly conducted. On the other hand, the absence of the quality control material indicates the improper implementation of sample preparation.

In some embodiments, the method may further comprise flowing the sample mixed with the control sample into a chamber for accommodating a solid substance whereby the control sample and the target entity in the sample are captured by the solid substance, prior to lysis.

In some embodiments, the sample may be filtered before being mixed with the control sample. In some embodiments, the lysing step includes exposing the control sample and the target entity to ultrasonic energy. In some embodiments, the lysing step includes homogenizing the control sample and the target entity with beads. In some embodiments, the control sample includes spores. In some embodiments, the mixing step includes disintegrating dry beads containing the control sample.

In some embodiments, the lysing step comprises contacting with a chemical lysis agent. In some embodiments, a marker nucleotide sequence is detected by amplifying the marker nucleotide sequence (with, for example, PCB), and detecting the amplified marker nucleotide sequence. According to some embodiments, the marker nucleotide sequence may be detected by determining whether or not a signal from a probe bound to the marker nucleotide sequence exceeds a limit value.

A reaction mixture in the reaction chamber of the amplification apparatus is exposed to a nucleic acid amplification condition. The amplification of RNA or DNA is known in the art [U.S. Pat. Nos. 4,683,195; 4,683,202; PCR Protocols: A Guide to Methods and Applications (Innis et. al., 1990)]. DNA amplification is generally performed through multiple cycles of thermally denaturing DNA, annealing a pair of oligonucleotide primers to a target sequence, and extending the annealed primers with a DNA polymerase. The primers are attached to opposite strands while DNA synthesis is performed between the primers using a polymerase to produce the target DNA fragment at a two-fold faster speed. In addition, because the nascent, extended strands are also complementary to each other and can be annealed with the primers, the quantity of DNA produced in each of the consecutive cycles is twice as large as that in the previous cycle. Accordingly, the target DNA fragment may be produced at a 2-fold rate per cycle, thus being accumulated in a total relative amount of $2^n$ (n being the number of cycles). PCR or ligase chain reaction (LCR) may be used to directly amplify a target sequence from mRNA, cDNA, genome libraries, or cDNA libraries. Isothermal amplification is also known, and may be used in the method of the present disclosure.

Nucleic acid amplification may be preferably carried out using a heat treatment device designed to heat and/or cool a reaction mixture to temperatures necessary for amplification. The heat treatment device may include at least one detector for detecting a marker nucleotide sequence and at least one target nucleotide sequence to be tested in the sample. Preferred is a heat treatment device embedded with an optical detector for amplifying and detecting nucleotide sequences in a reaction vessel (U.S. Pat. Nos. 6,369,893; 6,391,541). In addition, other known methods for controlling temperatures of the reaction mixture and for detecting a target sequence from the reaction mixture may be used in the present disclosure.

Further, the detection of a quality control material in a control sample and at least one quality control material in a sample to be tested is preferably conducted with a probe. In a preferred embodiment, a reaction vessel has at least one transparent or semi-transparent wall through which an optically detectable signal from the probe can pass. Preferably, the capture probe may be used in detecting and quantitating nucleic acid sequences. There are numerous assays utilizing nucleic acid-capturing probes. Some of the capture probes generate fluorescent signals that change with interaction with other molecules or moieties.

In another preferred method for detecting an amplified product, a fluorescent probe may consist of an oligonucleotide labeled with a fluorescent reporter dye. The dissociation of the capture probe increases the fluorescent intensity of the reporter dye.

In order to ensure the presence or absence of a target biomolecule in a sample, it is essential to control contamination during sample preparation. This is why the control sample should be subjected to the same treatment as a target entity of the test sample (e. g., target cells, spores, viruses or microorganisms containing a biomolecule of interest). The positive detection of the quality control material in the control sample indicates that the sample preparation process has been properly conducted. On the other hand, when the quality control material is not detected, the sample preparation is regarded as being improper and the test result of target nucleotide sequences are classified as "undetermined". Preferably, the detection of a quality control material may be achieved when the signal from the capture probes bound to a target probe meets or exceeds a limit value, for example, a predetermined limit value of fluorescence, that is, a minimal value regarded as being effective for a fluorescence assay.

The fluid controller may be controlled by a computer according to a desired protocol. The employment of a single value increases the possibility of improving the production yield because there is only one failure element. The integration of the fluid controller into other elemental members may yield a compact device (for example, a small cartridge) and makes it easy to automate fabrication and assembly processes. As stated above, such a system may be advantageously provided with a diluting and mixing function, an intermediate washing function, and a reliable pressurizing function. A fluid passage within the system is usually closed so as to prevent the contamination of the fluid in the system and to facilitate the reception and control of the fluid. The reaction vessel may be conveniently detached and changed with a fresh one. In some embodiments, it may be discarded.

The present disclosure provides a nucleic acid chip for analyzing receptors and nucleic acids of a biological sample, using aptamers, whereby the biological significance of the receptors and the nucleic acids can be determined.

The present disclosure provides a method and an apparatus for analyzing a biomolecule, comprising a structure designed to analyze the biological significance of the biomolecule using biomolecule information data, the structure comprising: a module in which the biomolecule information of a group of patients and the biomolecule information data of a control are received to construct a database; a module in which the input information data is used for pre-treatment in an analysis system; a module in which a patient module is created with the pre-treatment result; and a module in which the patient model is loaded into the system, and applied to a hospitalized patient or an outpatient to perform a diagnosis in a blind test manner; and evaluating the function of the system through a cross validation analysis.

The biological significance-predicting system using the biomolecule information data in accordance with the present disclosure is used for illustrative diagnosis, but is not limited thereto.

A huge amount of biomolecule information data with regard to various disease-related factors including cells, tissues, etc. can be produced in accordance with the present disclosure. The module in which the input data is used for pre-treatment in an analysis system is adapted for searching for factors having an influence on the health state of patients and for conducting feature selection using multivariate analysis. Feature selection is a process of selecting a subset of relevant features through dimensionality reduction or feature modification for accurate treatment and diagnosis.

For feature selection, unsupervised learning or supervised learning is employed according to whether or not class information is utilized for learning. In PCA (Principal Component Analysis) or ICA (Independent Component Analysis), typically utilized for unsupervised learning, features are selected in consideration of variables. Supervised learning is a method in which variables are selected using statistical significance between class information and variables or correlation between variables. In supervised learning, features are sequentially added or removed in forward or backward propagation, and important features can be selected after the function is examined upon the application of the resulting features to a classifier.

The module in which learning is conducted with the pre-treatment result to construct a patient model is designed to classify the selected features through suitable classifier.

Artificial neural networks, which find applications in a variety of fields including pattern recognition, function approximation, classification, etc., are employed in the present disclosure. An artificial neural network is structured to include multiple layers, nodes, and interconnection weights between neural networks. The neural network interlayer connection used in the present disclosure is of feed-forward type. Depending on input patterns, an interconnection weight for each node and an activation function are used to calculate an output value. When a calculated value is different from a measured value after an event is treated through the produced connective information, the error can be minimized by repetitive comparison between calculated values and measurements.

In the method and apparatus for analyzing a biomolecule according to the present disclosure, the construction of the patient model is performed using at least one selected from the group consisting of linear models, support vector machines, neural networks, classification and regression trees, ensemble learning methods, discriminant analysis, nearest neighbor method, Bayesian networks, and independent components analysis.

In consideration of the fact that accurate and comprehensive mechanisms are not defined for many diseases, case-based diagnosis is of great importance. However, conventional case-based machine learning inference systems conceived on the basis of specific machine learning techniques show poor accuracy, and there is therefore a need for improved systems. In addition, conventional systems are developed to utilize all of the learned clinical examination items only in diagnosing diseases, but do not provide importance and priority of individual clinical examination items according to diseases.

The present disclosure addresses a system for selecting clinical diagnosis and examination items, using case-based machine learning inference, the system comprising analyzing examination information of a new patient to make a preliminary diagnosis with the aid of a machine learning disease discriminator using a neural network trained with a case database of patients, and selecting a minimal number of important examination items for the final decision of an accurate disease. The construction of the patient model is performed using at least one selected from the group consisting of linear models, support vector machines, neural networks, classification and regression trees, ensemble learning methods, discriminant analysis, nearest neighbor method, Bayesian networks, and independent components analysis.

The practical application of the system may be achieved in two manners. For example, it may be structured as a stand-alone diagnosis system or as an integrated system in association with a conventional hospital information system, e.g., OCS, PACS, LIS, etc. For use in association with such a conventional hospital information system, the system should be structured according to HL7 and DICOM protocols. In conjunction with the early-stage model PMS (Patient Monitoring System), the system of the present disclosure exhibits highly accurate diagnosis. The system of the present disclosure may be developed into a diagnosis system of higher accuracy when designed to operate in association with various medical information systems such as OCS, EMR, and PACS in addition to PMS.

In the method and apparatus for analyzing a biomolecule, using an oligonucleotide in accordance with the present disclosure, the biological sample is at least one selected from the group consisting of cells, fungi, viruses, cell lines, and tissues.

Advantageous Effects

As described above, the use of oligonucleotides according to the present disclosure can analyze biomolecules in biological samples at high fluorescent sensitivity, with the consequent determination of the biological significance of the biomolecules. Further, the method and apparatus of the present disclosure allows for the analysis of various biomolecules in a single test, thereby effectively determining biological differences between individual persons, including phenotypic changes in the biological samples, susceptibility to diseases, and drug sensitivity.

DESCRIPTION OF DRAWINGS

FIG. 7 is an arrangement of the capture probes responsive to aptamers, mRNAs, mutant DNAs and methylated DNAs, all carrying either IL17 or IL17RA.

BEST MODE

Figure 1:
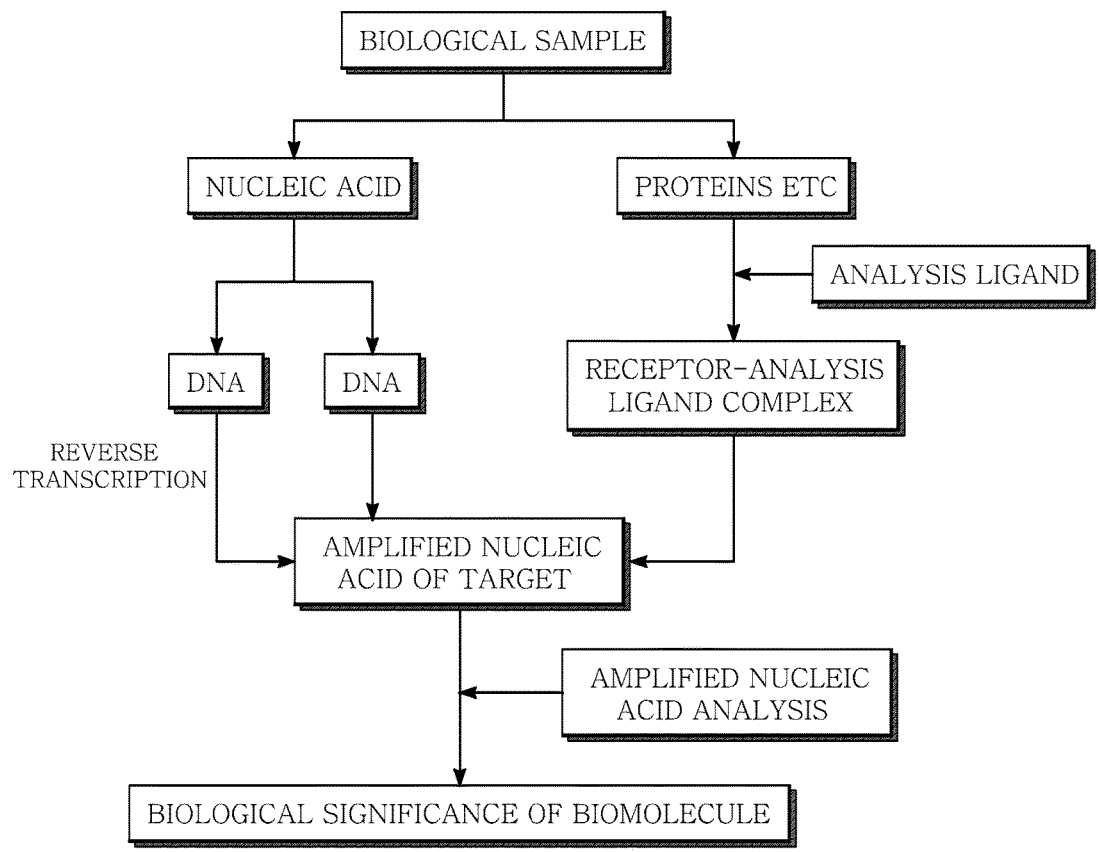
FIG. 1 is an overall flow diagram illustrating the determination of biological significance of a biomolecule in a biological sample by isolating nucleic acids and proteins separately, reacting the proteins with an analysis ligand to form a protein-analysis ligand complex, separating the nucleic acids into RNA and DNA, preparing a target DNA covering a target nucleic acid to be analyzed, and analyzing the target DNA with an oligonucleotide perfectly complementary to a specific region of the target nucleic acid.
Figure 2:
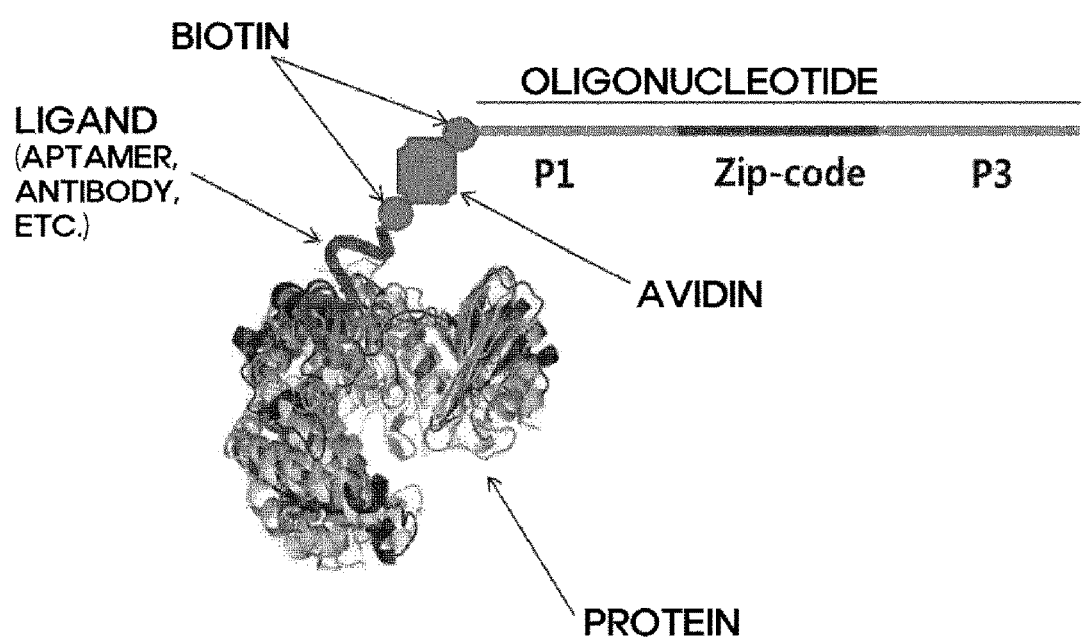
FIG. 2 is a schematic view of a complex between a receptor isolated from a biological sample and an analysis ligand.
Figure 3:
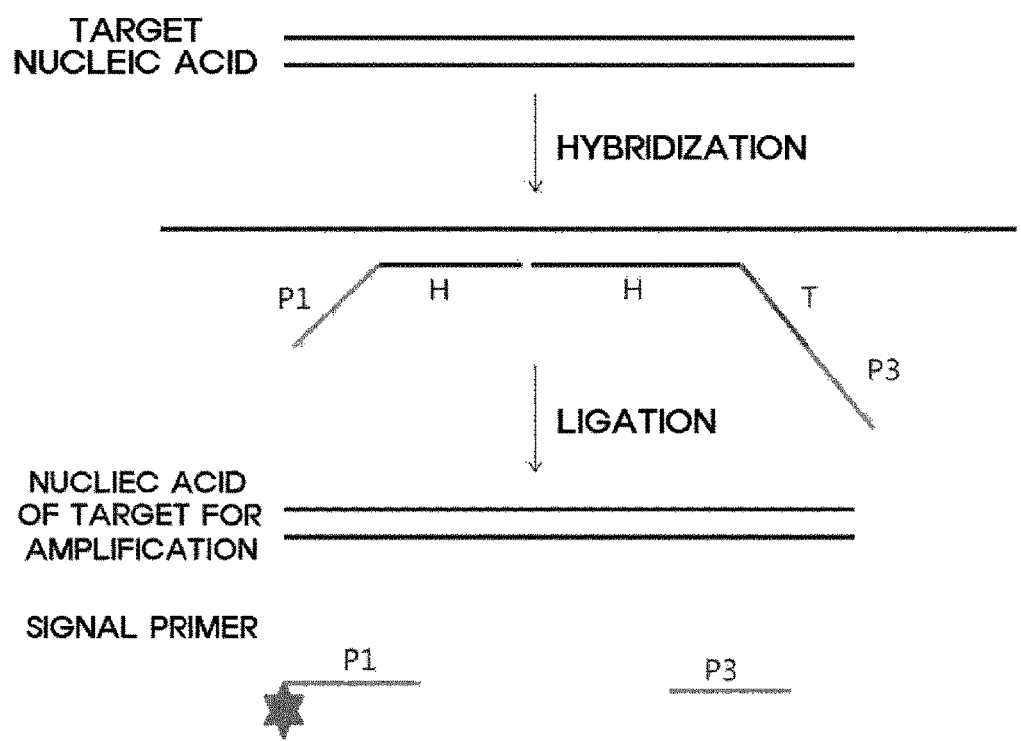
FIG. 3 is a view illustrating the quantitative analysis of RNA using the cDNA reversely transcribed the RNA.
Figure 4:
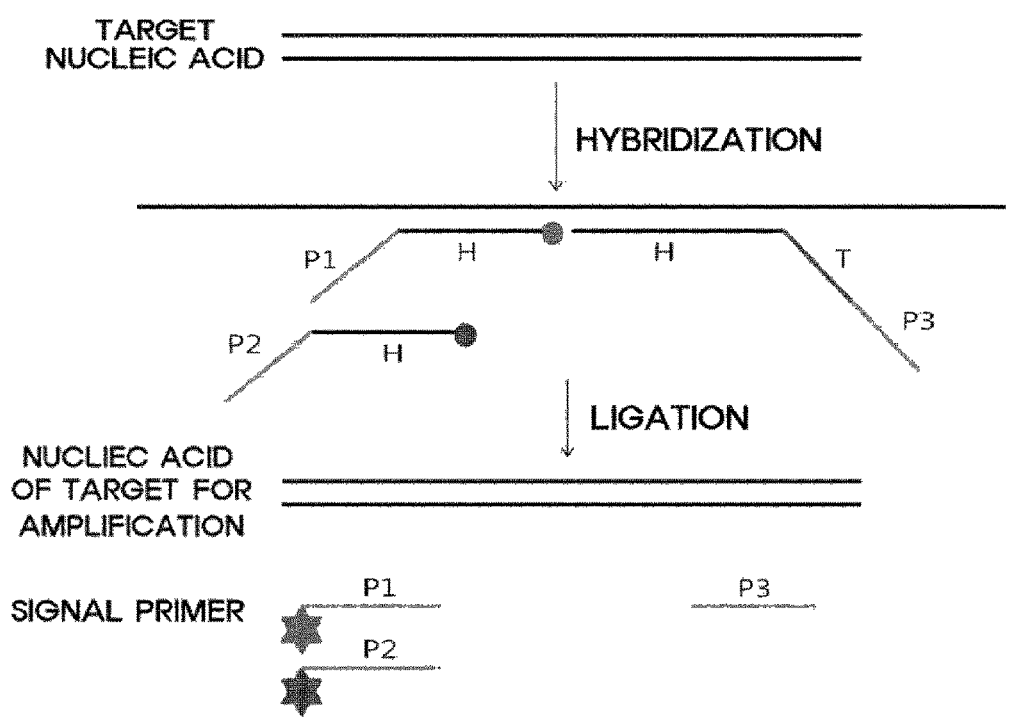
FIG. 4 is an overall flow view illustrating the analysis of the mutation of a target nucleic acid with oligonucleotides perfectly complementary to certain regions of a nucleic acid isolated from a biological sample.
Figure 5:
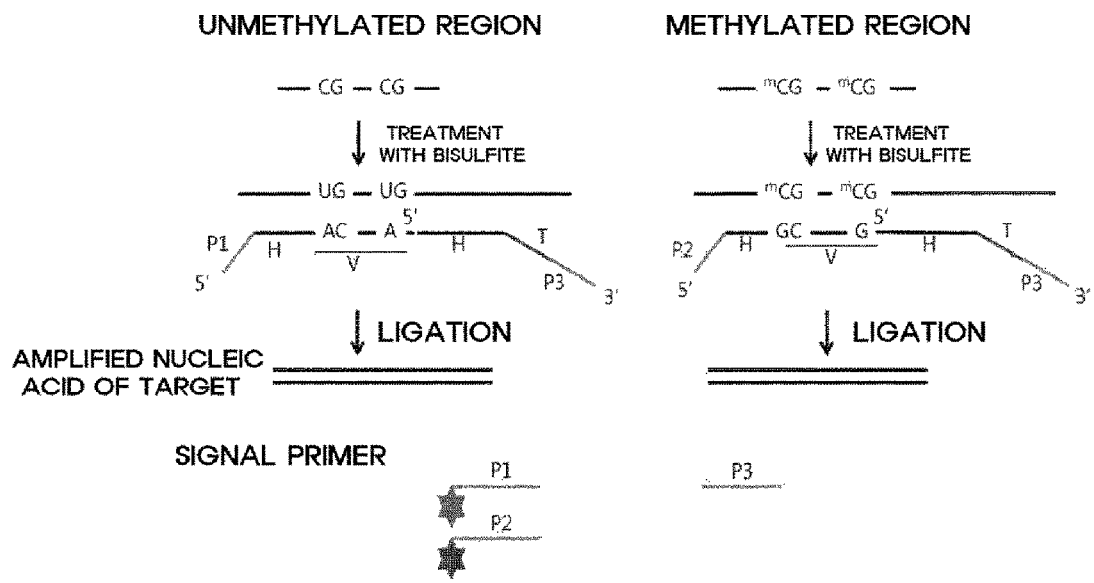
FIG. 5 is an overall flow view illustrating the analysis of the methylation of a target DNA isolate with oligonucleotides perfectly complementary to certain regions of the target DNA isolate.

Below, a detailed description will be given of standard materials, the preparation of nucleic acid chips, and a method for analyzing two or more different biomolecules in a biological sample, using the same, with reference to the accompanying drawings. The following Examples are set forth to illustrate, but are not to be construed as limiting the present invention.

As biomolecules, IL17 and IL17RA were used in the present disclosure. These biomolecules are analyzed at protein and nucleic acid levels in a single array assay for protein, mRNA, and DNA mutation.

IL-17, which is a cytokine produced the CD4+ T-cells, called Th17 cells, has an amino acid sequence represented as Accession code AAH67505 or NP002181. IL-17A or CTLA-8 is known as a member of the IL-17 family. An IL-17 receptor is a cell surface protein to which IL-17 binds. Within the scope of the IL-17 receptor family, IL-17RA, IL-17RB, IL-17RC, IL-17RD, and IL-17RE fall.

As used herein, the term "IL-17-mediated inflammatory disease" is intended to encompass all the diseases caused by IL-17 secreted from immune or inflammatory cells such as gamma/delta T cells, NK cells, macrophages, neutrophils, etc., in addition to Th17 cells, including respiratory diseases, gastrointestinal diseases, dermal diseases, vascular diseases, metabolic diseases, osteoarthritic diseases, and cerebral nerve diseases.

In detail, the respiratory diseases are exemplified by rhinitis, nasal polyp, sinusitis, asthma, bronchitis, chronic obstructive pulmonary disease, bronchiectasis, bronchiolitis, pneumonia, pulmonary fibrosis, lung cancer, etc. Examples of the gastrointestinal diseases include stomatitis, esophagitis, gastritis, gastric ulcer, inflammatory bowel disease, irritable bowel syndrome, cholangitis, pancreatitis, oral cancer, esophageal cancer, stomach cancer, colorectal cancer, cholangiocarcinoma, gallbladder cancer, and pancreatic cancer.

Representative among the vascular and metabolic diseases are arteriosclerosis, diabetes, and gout. The osteoarthritic diseases include rheumatoid arthritis, osteoarthritis, osteoporosis, etc. The cerebral nerve diseases include vascular dementia, Alzheimer's disease, neurodegenerative disease, etc.

In Examples of the present disclosure, IL17 and IL17RA were quantitatively analyzed at protein and RNA levels. Genetic information on IL17 and IL17RA is available from the GenBank Data System (http://www.ncbi.nlm.nih.gov) and their nucleotide sequences are identified (Accession number NM_002190 for IL17, and Accession number: NM_014339 for IL17RA)

For DNA mutation analysis, SNPs of IL17 and IL17RA were employed, and the genetic information thereof was found in http://www.ncbi.nlm.nih.gov/snp.

Nucleic acid methylation was analyzed at position IL17 promoter-144 (Thomas, R. M., et al., 2012, J Biol Chem. 287(30):25049-59.).

TABLE 1

| | Base Sequence of Specific Region(H) of Target Nucleic Acid | | | | |
|---|---|---|---|---|---|
| | Upstream Oligonucleotide (5'→3') | SEQ ID NO. | Downstream Oligonucleotide (5'→3') | SEQ ID NO. | # |
| β-actin mRNA | gggcgacgaggcccagagcaagaga | 1 | ggcatcctcaccctgaagtacccca | 61 | 1 |
| | cagatcatgtttgagaccttcaaca | 2 | ccccagccatgtacgttgctatcca | 62 | 2 |
| IL17 mRNA | ccctcaggaaccctcatccttcaaa | 3 | gacagcctcatttcggactaaactc | 63 | 3 |
| | taaccgaataccaataccaatccc | 4 | aaaaggtcctcagattactacaacc | 64 | 4 |
| IL17RA mRNA | ggagcagaagcctcccagccactag | 5 | ccttttgggctcagtctctccaata | 65 | 5 |
| | gagtacaggataccacaatgcactc | 6 | ttcctgcgtagagcacatgttccca | 66 | 6 |
| IL17 SNP | | | | | |
| rs10484879 | AAACTCATCGTGAAGTCAAACATTCAA | 7 | ATTGGAAGAAAGAGCTATAGAAAAT | 67 | 7 |
| | AAACTCATCGTGAAGTCAAACATTCAC | 8 | | | |
| rs8193038 | GGAATACTGTATATGTAGGATAGGAAA | 9 | TGAAAGCTTTGGTAGGTATTTAAGT | 68 | 8 |
| | GGAATACTGTATATGTAGGATAGGAAG | 10 | | | |
| rs8193037 | TGTCACCCCTGAACCCACTGCGACACA | 11 | CCACGTAAGTGACCACAGAAGGAGA | 69 | 9 |
| | TGTCACCCCTGAACCCACTGCGACACG | 12 | | | |
| rs8193036 | CCCCCCTGCCCCCCTTTTCTCCATCTC | 13 | CATCACCTTTGTCCAGTCTCTATCC | 70 | 10 |
| | CCCCCCTGCCCCCCTTTTCTCCATCTT | 14 | | | |
| rs4711998 | TGTATTCCTGAGAAGGAACTATTCTCA | 15 | AGGACCTGAGTCCAAGTTCATCTTA | 71 | 11 |
| | TGTATTCCTGAGAAGGAACTATTCTCG | 16 | | | |
| rs3819025 | TCATTGGTGGTGAGTCCTGCACTAACA | 17 | TGCGATGCTCTTGCTGATTTGGACC | 72 | 12 |
| | TCATTGGTGGTGAGTCCTGCACTAACG | 18 | | | |
| rs3819024 | AACACCTGGCCAAGGAATCTGTGAGGA | 19 | AAAGAAAGATCAAATGGAAAATCAA | 73 | 13 |
| | AACACCTGGCCAAGGAATCTGTGAGGG | 20 | | | |
| rs3804513 | CAAATGTATTTTGATCATTTGACTTCA | 21 | TACAAATAAGTCTCTGTTCTGTGGA | 74 | 14 |
| | CAAATGTATTTTGATCATTTGACTTCT | 22 | | | |

TABLE 1-continued

Base Sequence of Specific Region(H) of Target Nucleic Acid

| | Upstream Oligonucleotide (5'→3') | SEQ ID NO. | Downstream Oligonucleotide (5'→3') | SEQ ID NO. | # |
|---|---|---|---|---|---|
| rs3748067 | TGGGCTGAACTTTTCTCATACTTAAAA<br>TGGGCTGAACTTTTCTCATACTTAAAG | 23<br>24 | TTCGTTCTGCCCCATCAGCTCC<br>TTT | 75 | 15 |
| rs2275913 | CTGCCCTTCCCATTTTCCTTCAGAAGA<br>CTGCCCTTCCCATTTTCCTTCAGAAGG | 25<br>26 | AGAGATTCTTCTATGACCTCATT<br>GG | 76 | 16 |
| rs1974226 | CTGAACTTTTCTCATACTTAAAGTTCA<br>CTGAACTTTTCTCATACTTAAAGTTCG | 27<br>28 | TTCTGCCCCATCAGCTCCTTTC<br>TGG | 77 | 17 |
| IL17RA SNP | | | | | |
| rs151315255 | GATGGCCTGCCTGCGGCTGACCTGATC<br>GATGGCCTGCCTGCGGCTGACCTGATT | 29<br>30 | CCCCCACCGCTGAAGCCCAGG<br>AAGG | 78 | 18 |
| rs139412425 | TGGATCATCTACTCAGCCGACCACCC<br>TGGATCATCTACTCAGCCGACCACCC K | 31<br>32 | CTCTACGTGGACGTGGTCCTG<br>AAAT | 79 | 19 |
| rs6518661 | CTGTCACTAAGGAGTTAACCCCCGCA A<br>CTGTCACTAAGGAGTTAACCCCCGCA G | 33<br>34 | AGCAGTTTTTTCATCACATCTCT<br>GA | 80 | 20 |
| rs6518660 | CATAGTAGATAGCAATCTATTCAACCA<br>CATAGTAGATAGCAATCTATTCAACCG | 35<br>36 | TTTCTAGTTTGATGGACATTTAG<br>AT | 81 | 21 |
| rs5748864 | gcaagttaggattagagggctgggacA<br>gcaagttaggattagagggctgggacG | 37<br>38 | tttagccccacccctttacccatca | 82 | 22 |
| rs4819554 | TGGGAAGTAACGACTCTCTTAGGTGC A<br>TGGGAAGTAACGACTCTCTTAGGTGC G | 39<br>40 | GCTGGGACACAGTCTCACAGA<br>CCAG | 83 | 23 |
| rs2241049 | GCATGGGAGGACCTATGGGAGGTTCC A<br>GCATGGGAGGACCTATGGGAGGTTCC G | 41<br>42 | ATAACATTCAGTAGCATCTCGG<br>CCA | 84 | 24 |
| rs2241046 | ATGCTATTTTCCCTTTTTCCTCTGTTC<br>ATGCTATTTTCCCTTTTTCCTCTGTTT | 43<br>44 | TCATTGCAGAACCAATTCCGGG<br>TAA | 85 | 25 |
| rs2229151 | CACCCCCTCTACGTGGACGTGGTCCT A<br>CACCCCCTCTACGTGGACGTGGTCCT G | 45<br>46 | AAATTCGCCCAGTTCCTGCTCA<br>CCG | 86 | 26 |
| rs882643 | ACGCTTTCCCCAACCACAATCCTTCAC<br>ACGCTTTCCCCAACCACAATCCTTCAG | 47<br>48 | CTCAGGCATCTCCTCGGGGAT<br>CCCC | 87 | 27 |
| rs879577 | TCAGCGGTGGGGGATCAGGTCAGC CA<br>TCAGCGGTGGGGGATCAGGTCAGC CG | 49<br>50 | CAGGCAGGCCATCTAAGGAAA<br>CAAG] | 88 | 28 |
| rs879576 | TGGTCGGCTGAGTAGATGATCCAGAC C<br>TGGTCGGCTGAGTAGATGATCCAGAC T | 51<br>52 | TTCCTGGGCTTCAGCGGTGGG<br>GGGA | 89 | 29 |
| rs879576 | TGGTCGGCTGAGTAGATGATCCAGAC C<br>TGGTCGGCTGAGTAGATGATCCAGAC T | 53<br>54 | TTCCTGGGCTTCAGCGGTGGG<br>GGGA | 90 | 30 |
| rs721930 | GTTCTGAGGGGTGATTAGGGAGGAGA C<br>GTTCTGAGGGGTGATTAGGGAGGAGA G | 55<br>56 | TTTAGTTTAACTTGGAGTCCTTC<br>AG | 91 | 31 |

TABLE 1-continued

Base Sequence of Specific Region(H) of Target Nucleic Acid

| | Upstream Oligonucleotide (5'→3') | SEQ ID NO. | Downstream Oligonucleotide (5'→3') | SEQ ID NO. | # |
|---|---|---|---|---|---|
| IL17 Aptamer | ggucuagccggaggaguc | 57 | aguaaucgguagacc | 92 | 32 |
| IL17RA Aptamer | ACGCGCTAGGATCAA | 58 | AGCTGCACTGAAGTG | 93 | 33 |
| IL17 methylation (promoter at position 144) | tcaaatcaattttaacatta tctacaacaag<br>tcaaatcaattttaacatta tctacaacaaa | 59<br><br>60 | gtcatacttgtgggctgga gaccaaaagcc | 94 | 34 |

TABLE 2

Capture Probes and Complementary Sequences thereof (zip-code base sequences directing ligands)

| # | Capture Probe (5'→3')(53) | SEQ ID NO. | Complementary (5'→3') | SEQ ID NO. |
|---|---|---|---|---|
| 1 | GATTTGTATTGATTGAGATTAAAG | 95 | CTTTAATCTCAATCAATACAAATC | 129 |
| 2 | TGATTGTAGTATGTATTGATAAAG | 96 | CTTTATCAATACATACTACAATCA | 130 |
| 3 | GATTGTAAGATTTGATAAAGTGTA | 97 | TACACTTTATCAAATCTTACAATC | 131 |
| 4 | GATTTGAAGATTATTGGTAATGTA | 98 | TACATTACCAATAATCTTCAAATC | 132 |
| 5 | GATTGATTATTGTGATTTGAATTG | 99 | CAATTCAAATCACAATAATCAATC | 133 |
| 6 | GATTTGATTGTAAAGATTGTTGA | 100 | TCAACAATCTTTTACAATCAAATC | 134 |
| 7 | ATTGGTAAATTGGTAAATGAATTG | 101 | CAATTCATTTACCAATTTACCAAT | 135 |
| 8 | GTAAGTAATGAATGTAAAAGGATT | 102 | AATCCTTTTACATTCATTACTTAC | 136 |
| 9 | GTAAGATGTTGATATAGAAGATTA | 103 | TAATCTTCTATATCAACATCTTAC | 137 |
| 10 | TGTAGATTTGTATGTATGTATGAT | 104 | ATCATACATACATACAAATCTACA | 138 |
| 11 | GATTAAAGTGATTGATGATTTGTA | 105 | TACAAATCATCATCACTTTTAATC | 139 |
| 12 | AAAGAAAGAAAGAAAGAAAGTGTA | 106 | TACACTTTCTTTCTTTCTTTCTTT | 140 |
| 13 | TTAGTGAAGAAGTATAGTTTATTG | 107 | CAATAAACTATACTTCTTCACTAA | 141 |
| 14 | AAAGTAAGTTAAGATGTATAGTAG | 108 | CTACTATACATCTTACTATACTTT | 142 |
| 15 | TGAATTGATGAATGAATGAAGTAT | 109 | ATACTTCATTCATTCATCAATTCA | 143 |
| 16 | TGATGATTTGAATGAAGATTGATT | 110 | AATCAATCTTCATTCAAATCATCA | 144 |
| 17 | TGATAAAGTGATAAAGGATTAAAG | 111 | CTTTAATCCTTTATCACTTTATCA | 145 |
| 18 | TGATTTGAGTATTTGAGATTTTGA | 112 | TCAAAATCTCAAATACTCAAATCA | 146 |
| 19 | GTATTTGAGTAAGTAATTGATTGA | 113 | TCAATCAATTACTTACTCAAATAG | 147 |
| 20 | GATTGTATTGAAGTATTGTAAAAG | 114 | CTTTTACAATACTTCAATACAATC | 148 |
| 21 | TGATTTGAGATTAAAGAAAGGATT | 115 | AATCCTTTCTTTAATCTCAAATCA | 149 |
| 22 | TGATTGAATTGAGTAAAAGGATT | 116 | AATCCTTTTACTCAATTCAATCA | 150 |
| 23 | AAAGTTGAGATTTGAATGATTGAA | 117 | TTCAATCATTCAAATCTCAACTTT | 151 |
| 24 | GTATTGTATTGAAAAGGTAATTGA | 118 | TCAATTACCTTTTCAATACAATAC | 152 |
| 25 | TGAAGATTTGAAGTAATTGAAAAG | 119 | CTTTTCAATTACTTCAAATCTTCA | 153 |

TABLE 2-continued

Capture Probes and Complementary Sequences thereof (zip-code base sequences directing ligands)

| # | Capture Probe (5'→3') (53) | SEQ ID NO. | Complementary (5'→3') | SEQ ID NO. |
|---|---|---|---|---|
| 26 | TGAAAAAGTGTAGATTTTGAGTAA | 120 | TTACTCAAAATCTACACTTTTCA | 154 |
| 27 | AAAGTTGAGTATTGATTTGAAAAG | 121 | CTTTTCAAATCAATACTCAACTTT | 155 |
| 28 | TTGATAATGTTTGTTTGTTTGTAG | 122 | CTACAAACAAACAAACATTATCAA | 156 |
| 29 | AAAGAAAGGATTTGTAGTAAGATT | 123 | AATCTTACTACAAATCCTTTCTTT | 157 |
| 30 | GTAAAAAGAAAGGTATAAAGGTAA | 124 | TTACCTTTATACCTTTCTTTTTAC | 158 |
| 31 | GATTAAAGTTGATTGAAAAGTGAA | 125 | TTCACTTTTCAATCAACTTTAATC | 159 |
| 32 | GTAGATTAGTTTGAAGTGAATAAT | 126 | ATTATTCACTTCAAACTAATCTAC | 160 |
| 33 | AAAGGATTAAAGTGAAGTAATTGA | 127 | TCAATTACTTCACTTTAATCCTTT | 161 |
| 34 | TGAAATGAATGAATGATGAAATTG | 128 | CAATTTCATCATTCATTCATTTCA | 162 |

TABLE 3

Universal PCR primers

| Forward (5'→3') | SEQ ID NO. | Backward (5'→3') | SEQ ID NO. |
|---|---|---|---|
| P1: 5'-ACTTCGTCAGTAACGGAC-3' | 163 | P3: 5'-GTCTGCCTATAGTGAGTC-3' | 165 |
| P2: 5'-GAGTCGAGGTCATATCGT-3' | 164 | | |

Example 1: Preparation of Biomolecule

Biomolecules were extracted from cells or a tissue sample containing cells, with the aid of an AllPrep DNA/RNA/Protein Mini kit (Qiagen. USA). In this Example, cartilage tissue (Promocell, Germany) was used as the source of the biomolecules. The cartilage tissue was lysed and homogenized in a buffer provided by the manufacturer, and was then passed through a column that was designed to allow selective binding of genomic DNA. The column was washed, and DNA was eluted from the column by spinning. After the addition of ethanol thereto, the flow-through from the AllPrep DNA spin column was applied to an RNA spin column, in which total RNA was bound to the membrane. The RNA bound to the membrane was eluted by washing. A buffer for protein precipitation was added to the through-flow from the RNA spin column, and the precipitated proteins were pelleted by centrifugation.

Example 2: Preparation of Ligand for Analysis 2-1. Antigen and Aptamer Analysis Ligands For preparation of a protein-antibody analysis ligand complex to be used in the quantitative analysis of a specific protein in the cartilage tissue, biotinylated antibodies against human IL17 (Catalog No. BAF317) and IL17RA (Catalog No. BAF177) were purchased from R&D Systems, USA.

In addition, for preparation of a protein-aptamer complex to be used in the quantitative analysis of a specific protein in the cartilage tissue was prepared, respective aptamers binding specifically to IL17 (Korean Patent No. 10-1276519-0000) and IL17RA (Chen, L., et al., 2011, Osteoarthritis and Cartilage 19; 711~718) were single-stranded nucleic acids with the nucleotide sequences given in Table 4, below. Biotinylated IL17 and IL17RA aptamers were chemically synthesized (Bioneer. Korea).

TABLE 4

Nucleotide Sequences of IL17 and IL17RA Aptamers

| Aptamer Name | Base Sequence (5'→3') | SEQ ID NO. |
|---|---|---|
| IL17 | GGUCUAGCCGGAGGAGUCAGUAAUCGGUAGACC | 166 |
| IL17RA | ACGCGCTAGGATCAAAGCTGCACTGAAGTG | 167 |

A biotinylated oligonucleotide used as a member of the antibody or aptamer analysis ligand for the quantitative analysis of a protein of interest is represented by the following general formula I:

5'-Biotin-P1-T-P3-3'    (I)

wherein,

P1 is a region complementary to a forward primer of a pair of primers carrying a detection signal, T is a region, complementary to a capture probe, which is designed to serve as a probe in a hybridization reaction, discriminating a target protein, or a single strand nucleic acid representing a target protein, and P3 is a region complementary to a backward primer of the pair of primers carrying the detection signal.

The biotinylated antibody and the biotinylated aptamer were connected with the biotinylated oligonucleotide through avidin to afford two conjugates, which are termed an antibody analysis ligand and an aptamer analysis ligand, respectively.

2-2. Upstream and Downstream Oligonucleotides 2-2-1. Quantitative Analysis of Nucleic Acid For use in the quantitative analysis of nucleic acids, an upstream oligonucleotide was designed to have the structure of the following Formula II:

5'-P1-H-3'  (II)

wherein,

P1 is a sequence region complementary to a forward primer of a pair of primers carrying a detection signal; and H is a sequence region complementarily hybridizable with a target nucleic acid.

A downstream oligonucleotide was designed to have the structure of the following Formula III:

5'-H-T-P3-3'  (III)

wherein,

H is a sequence region complementary to the target nucleic acid at a site downstream of the 3' end of the upstream oligonucleotide, T is a region, perfectly complementary to a capture probe, which is designed to serve as a probe in a hybridization reaction, discriminating a target nucleic acid, or a single strand nucleic acid representing a target nucleic acid, and P3 is a region complementary to a backward primer of the pair of primers carrying the detection signal.

In Formulas II and III, H may be a nucleotide sequence specific for an mRNA for β-actin, IL17, IL17R, etc., and the sequences are listed in Table 1. The sequences available for T are given in Table 2, and for P1 and P3 in Table 3. With reference to these sequences, upstream and downstream oligonucleotides for nucleic acid mutation analysis were chemically synthesized (Bioneer, Korea).

2-2-2. Nucleic Acid Mutation Analysis

For use in the mutation analysis of a target nucleic acid, an upstream oligonucleotide sequence was designed to have the following formula IV:

5'-P2-H-V-3'  (IV)

wherein,

P2 is a region to which a forward primer carrying a detection signal complementarily binds, H is a region complementarily hybridizable with a target nucleic acid, and V is a region complementarily hybridizable with the mutant sequence of the target nucleic acid. In this context, the upstream oligonucleotide may be composed of two or more different oligonucleotides.

For use in the mutation analysis of a target nucleic acid, a downstream oligonucleotide sequence was designed to have the following formula V:

5'-H-T-P3-3'  (V)

wherein,

H is a sequence region complementary to the target nucleic acid at a site downstream of the mutant region of the target nucleic acid, T is a region, complementary to a capture probe, which is designed to serve as a probe in a hybridization reaction, discriminating a target mutant nucleic acid, or a single strand nucleic acid representing a target mutant nucleic acid, and P3 is a region complementary to a backward primer.

In Formulas IV and V, H may be a nucleotide sequence specific for SNP of IL17, SNP of IL17RA, methylated IL17, etc., and the sequences are listed in Table 1. Sequences available for T are given in Table 2, and for P1 and P3 in Table 3. With reference to these sequences, upstream and downstream oligonucleotides for nucleic acid mutation analysis were chemically synthesized (Bioneer, Korea).

Example 3: Preparation of Quality Control Single-Stranded Nucleic Acid

Reference materials include five different plant-specific proteins A, B, C, D, and E, obtained from the website http://genomics.msu.edu/plant_specific/ (see Table 5).

TABLE 5

| | Plant-Specific Protein | | |
|---|---|---|---|
| | Locus | Description | Accession number |
| A | At1g65390.1 | defense/immunity protein | GO:0003793 |
| B | At5g39310.1 | cell elongation | GO:0009826 |
| C | At4g15910.1 | Drought-Induced Protein (Di21) | GO:0009414 |
| D | At1g12860.1 | Bhlh Protein | GO:0003677 |
| E | At4g02530.1 | Chloroplast Thylakoid Lumen Protein | GO:0009543 |

The five selected plant-specific proteins were expressed in *E. coli* expression systems, and used in the standard SELEX method (Ellington, A. D. and J. W. Szostak. 1990. In vitro selection of RNA molecules that bind specific ligands. Nature 346: 818-822; Gold, L., P. Allen, J. Binkley, D. Brown, D. Schneider, S. R. Eddy, C. Tuerk, L. Green, S. Macdougal, and D. Tasset 1993. RNA: the shape of things to come, pp. 497-510. In: R. F. Gestelend and J. F. Atkins (eds.). The RNA World, Cold Spring Harbor Press, Cold Spring Harbor, N.Y.) to acquire single-stranded nucleic acids capable of specifically binding to the reference materials.

The single-stranded nucleic acids were designated as quality control single-stranded nucleic acids. After being biotinylated, the quality control single-stranded nucleic acid was conjugated with a biotinylated oligonucleotide represented by Formula I via avidin to afford a structure for the analysis of the reference materials. For the purpose of convenience, the structure was termed a "quality control ligand".

Example 4: Preparation of Nucleic Acid Sample 4-1. Protein 4-1-1. Antibody Analysis Ligand Each well of microtiter plates to which the protein solution prepared from the cartilage tissue was added in an amount of 100 µl was coated at 4° C. overnight or at 37° C. for 2 hrs with a 0.05M carbonate buffer (pH 9.6).

After incubation for 30 min at room temperature with avidin (7.2 µg/ml), 100 µl of a biotinylated antibody (10 µg/ml) was mixed with the biotinylated oligonucleotide to produce an antibody-avidin-oligonucleotide, termed an antibody analysis ligand.

The wells were blocked with phosphate buffered saline (180 µl/well) containing 3% skimmed milk, 0.1 mM ethylene diamine tetraacetate, and 0.02% sodium azide, and washed twice with phosphate buffered saline-Tween 20, followed by incubation at 37° C. for 2 hrs with 100 µl of the antibody analysis ligand (10 µg/ml). The wells were washed five times for 5 min with Tween-PBS, and then four times for 5 min with distilled water to remove non-specifically bound, biotinylated oligonucleotides. The content in each well was transferred to a 500 µl Eppendorf tube and used as a nucleic acid sample.

4-1-2. Aptamer Analysis Ligand

The biotinylated IL17 aptamer (10 µg/ml) 100 µl and the biotinylated IL17RA aptamer (10 µg/ml) 100 µl, prepared as described above, were each incubated at room temperature for 30 min with avidin (7.2 µg/ml) and then with the biotinylated oligonucleotide (10 µg/ml) to give an aptamer-avidin-oligonucleotide, termed an aptamer analysis ligand. The proteins separated from the cartilage tissue were immobilized onto a nitrocellulose disk, which was then treated for 30 min with the IL17 and IL17RA aptamer analysis ligands in a SELEX buffer to form a protein-aptamer analysis ligand complex. It was purified by washing to remove non-specifically bound aptamers. The pure protein-aptamer analysis ligand complex was used as a nucleic acid sample.

4-2. RNA

For quantitative analysis and mutation analysis of a particular RNA, total RNA 10 ng, $dT_{20}$ primer (100 µmoles/20 µl reaction buffer, Bioneer, Korea), MMLV reverse transcriptase (200 U/20 µl reaction buffer, Bioneer, Korea), 10× Reaction buffer 2 µl, RNasin (15 U/20 µl reaction buffer, Promega) and betaine (500 mM/20 µl reaction buffer, Sigma) were mixed to give a reverse transcription solution. Using this solution, reverse transcription was started under a single temperature condition of 42° C. or 52° C. for 10, 20, 40, or 60 min, followed by 2, 4, 8, or 12 cycles of 37° C. for 2 min and 50° C. for 3 min, or 2, 4, 8, or 12 cycles of 37° C. for 1 min, 47° C. for 3 min, and 55° C. for 1 min. The cDNA thus obtained was used as a nucleic acid sample.

4-3. DNA Mutation

A particular DNA was analyzed for mutation. To this end, genomic DNA was extracted from the cartilage tissue using a kit, and used as a nucleic acid sample for the analysis of DNA mutation after determining its concentration using NanoDrop.

4-4. Methylation

A certain DNA was analyzed for methylation. To this end, genomic DNA was extracted from the cartilage tissue using a kit, and measured for concentration using NanoDrop. Then, about 1~2 µg of the extracted DNA was mixed with 0.5 N NaOH to a concentration of 16 mM, followed by denaturing the DNA into a single strand form at 37° for 15 min. Subsequently, the denatured DNA was incubated at 56° C. for 16 hrs in the presence of 3.5M sodium bisulfite and 0.01 M hydroquinone. The bisulfite-modified DNA was precipitated with ethanol and eluted at 50° C. in deionized water. NaOH was added to a concentration of 0.1 M and incubated at room temperature for 15 min to desulfonate DNA at cytosine residues. After precipitation in ethanol, the DNA pellet thus obtained was dissolved at 30° C. in deionized water before storage at −20° C. The DNA was used as a nucleic acid sample for the analysis of methylation.

Example 5: Preparation of Nucleic Acid Sample for Amplification

From the target nucleic acid-containing samples of cartilage tissue origin, including the RNA sample, the genomic DNA sample, and the protein-analysis ligand complex, nucleic acids for use in amplification reactions were prepared as follows.

The protein-analysis ligand complex having the oligonucleotide prepared for quantitative analysis of the protein in Example 4 was itself used as a nucleic acid sample for amplification.

From the nucleic acid samples of Example 4, including the cDNA reversely transcribed from the RNA extract, the genomic DNA for DNA mutation analysis, and the bisulfate-modified DNA that reflected the information of methylation on genomic DNA, nucleic acid samples for amplification were prepared as follows.

A mixture of the nucleic acid samples was hybridized with the upstream and the downstream oligonucleotide to make a partially double-stranded nucleic acid which was then converted into a fully double-stranded nucleic acid by extension from the upstream oligonucleotide to the downstream oligonucleotide. The double-stranded DNA was used as a sample for amplification.

The following 10-ml reaction solution was subjected to PCR, which started by denaturing at 95° C. for 5 min, and was then performed with 10 cycles of 95° C. for 1 min, 70° C. for 1 min, 68° C. for 1 min, 66° C. for 1 min, and 64° C. for 3 min.

The 10-ml reaction solution contained 20 mM TrisHCl (pH 7.6), 25 mM sodium acetate, 10 mM magnesium acetate, 1 mM dithiothreitol, 1 mM NAD+, 0.1% Triton X-100, the upstream and the downstream oligonucleotide prepared in Example 2 (500 pM each), 1 unit Taq DNA ligase (New England Biolabs, MA, USA), and 100 µg of the mixture of the nucleic acid samples.

Example 6: Amplification

In a PCR apparatus, amplification started by denaturing at 95° C. for 3 min and then proceeded with 42 cycles of 95° C. for 10 sec, 56° C. for 10 sec, and 72° C. for 20 sec. The 25-ml reaction solution used in the amplification contained 10 mM TrisHCl (pH 8.6), 50 mM KCl, 2.5 mM MgCl2, 5% (V/V) glycerin, 1 U Taq DNA polymerase, 1 µmol forward signal primers (P1 alone for wild-type target DNA, P1 and P2 for mutant DNA), 20 µmol reverse signal primer (P3), and 2 ml of the reaction solution of Example 5.

Primers for analyzing a wild-type target nucleic acid were composed of a forward primer, which is complementary to the P1 region of the analysis ligand or upstream oligonucleotide and which is labeled with Cy3, generating a detection signal, and a backward primer complementary to the P3 region.

For analyzing a mutant target nucleic acid, at least two forward primers, composed of a Cy3-labeled primer complementary to the P1 region and a Cy5-labeled primer complementary to the P2 region, were used while the backward primer was a universal primer complementary to the P3 region. The nucleotide sequences of these PCR primers are given in Table 2.

Example 7: Array Construction

For the capture probes for discriminating target nucleic acids, oligomers having nucleotide sequences corresponding to target nucleic acids were suggested in Table 2. After being chemically synthesized (Bioneer, Korea), the capture probes were patterned on an array.

The upstream and downstream oligonucleotides of Table 1 were designed to be perfectly complementary to a specific region of the target nucleic acid which the capture probe of Table 2 represents.

Briefly, the No. 1 capture probe of Table 2 represents β-actin mRNA, which is perfectly complementary to the No. 1 upstream and downstream oligonucleotides of Table 1, while the No. 3 capture probe of Table 2 represents IL17 mRNA that is perfectly complementary to the No. 3 upstream and downstream oligonucleotides of Table 1.

On an UltraGAPS™ Coated Slide (Corning), which is a slide coated with GAPS (Gamma Amino Propyl Silane), capture single-stranded nucleic acids were immobilized in a predetermined pattern to construct a nucleic acid chip. For the nucleic acid chip construction, a Microarrayer system (GenPak) was employed, in which pins were used to place spots at a center-to-center spacing of 150 μm. Each capture single-stranded nucleic acid was dissolved at a desired concentration in a standard solution. During spotting, a humidity of 70% was maintained within the array. The spotted slides were left for 24-48 hrs in a humidified chamber, and then baked in a UV crosslinker. After the capture single-stranded nucleic acids were immobilized onto the glass slides in a well-known manner, the slides were dried by spinning, and stored in darkness. As described, a slide glass was used as a support in array construction. Here, the support may be coated with amine or aldehyde. For example, the capture probes were arrayed and fixed in regular patterns on an UltraGAPS™ Coated Slide (Corning), which is a slide coated with GAPS (Gamma Amino Propyl Silane), to construct an array.

The array construction may be achieved using, for example, a Microarrayer system. Each capture probe was dissolved at a predetermined concentration in a buffer and spotted while the array was maintained a humidity of 70 to 80%.

After being maintained in a humidified chamber, the spotted slides were baked in a UV crosslinker.

As described, the array according to the present disclosure is constructed by immobilizing the captured single-stranded nucleic acids onto glass slides in a well-known manner, and drying the slides through centrifugation. The array may be stored in a dark condition before use.

Example 8: Array Hybridization and Analysis

Target probes, each carrying the base sequence of a specific region of a target nucleic acid, and a base sequence perfectly complementary to a capture probe, were applied to the array, hybridized at 60° C. for 4~12 hrs with the capture probes, and washed at 42° C. with 0.1×SSC buffer.

The hybridization buffer contained 1 M sodium chloride, 0.3 M sodium citrate, 0.5% SDS or 100 μg/ml salmon sperm DNA, and 0.2% bovine serum albumin or single-stranded nucleic acid. Following hybridization, the array was stepwise washed with wash buffers.

The wash buffers contained compositions of 1×SSC+ 0.2% SDS, 1×SSC+0.2% SDS, 0.5×SSC+0.2% SDS, and 0.01×SSC+0.2% SDS, and were used in that order at 42° C. for 30 min for sequential wash steps.

Example 9: Scanning and Analysis of Spot on DNA Chip

Following washing in Example 6, the glass slides were dried by centrifugation, and scanned using a laser scanner (GenePix4000, Axon) that performs excitation at the 635 nm (Cy5) wavelength. The images thus generated were stored as TIFF (multi-image Tagged Image File Format) files, and analyzed using suitable image analysis software (GenePix Pro 3.0, Axon).

The signal intensity (unit: quanta) at each spot was used, exclusive of a background signal. Here, the background signal means a local background acquired from four spots around a spot of interest. Generally, when at least 90% of pixels in a spot show a higher signal intensity than a background signal+2 standard deviations (S.D.), the spot is included in data analysis; otherwise, it is classified as a bad spot and not included in data analysis.

Signal intensity was normalized against variations according to labeling efficiency using internal standard (IS) intensity (e.g., Normalized Intensity=Probe Intensity/IS intensity). In the case of monolabeling, the signal intensity of Cy5 channels was recorded. When spotting is conducted two or more times, mean values are used. For the signal intensity (S) of target single-stranded nucleic acids, a median value of individual spot pixel intensities (median value of pixel-by-pixel) was used. The signal intensity (S) was normalized against variation in labeling efficiency using internal standard (IS) signals.

$$S'(\text{normalized value}) = S \text{ (Cy5-reference)} \times (\text{Cy5-IS}).$$

As mentioned above, the analysis results for the pixel density can be plotted against the amounts of the sample to determine the correlation therebetween.

Figure 6:
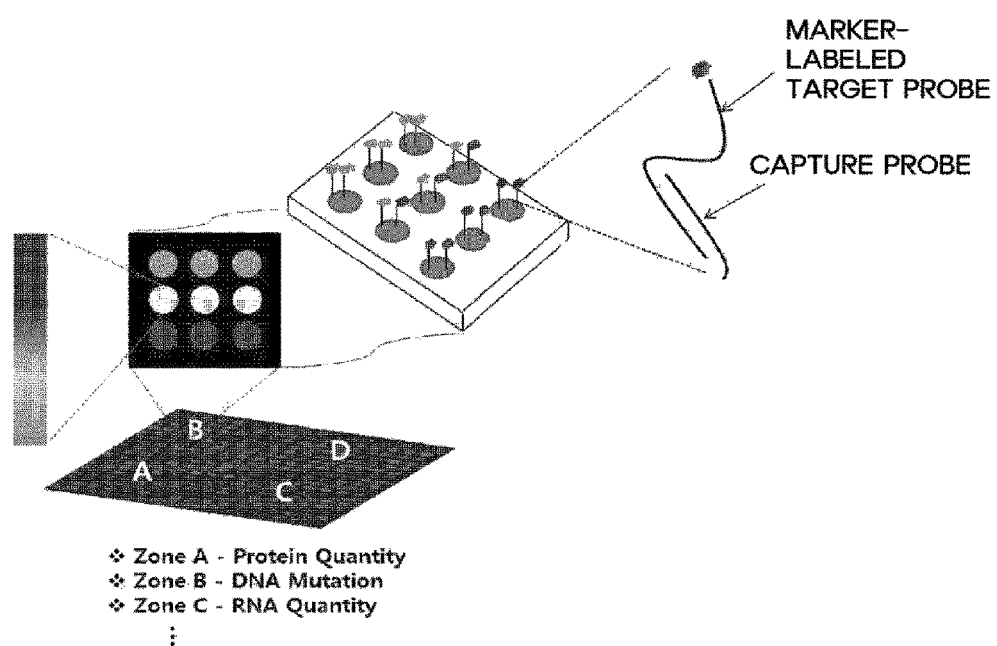
FIG. 6 is a view illustrating the analysis of biomolecules through signals generated upon hybridization between a marker-labeled target probe and a capture probe on an array.

As can be seen in FIG. 6, in which an experimental result is shown in accordance with an embodiment of the present disclosure, spot fluorescence intensities on the array allow for the qualitative and quantitative analysis of proteins, mRNAs, DNA mutation and DNA methylation.

FIG. 7 is an array image of capture probes hybridized with target probes that were prepared by forming partial double-stranded nucleic acids with oligonucleotides for analyzing proteins, mRNA and wild-type or mutant DNA carrying IL17 or IL17RA, extending them to give complete double-stranded nucleic acids, and amplifying target genes in the presence of signal primers through PCR, with the double-stranded nucleic acids serving as templates.

Figure 8:
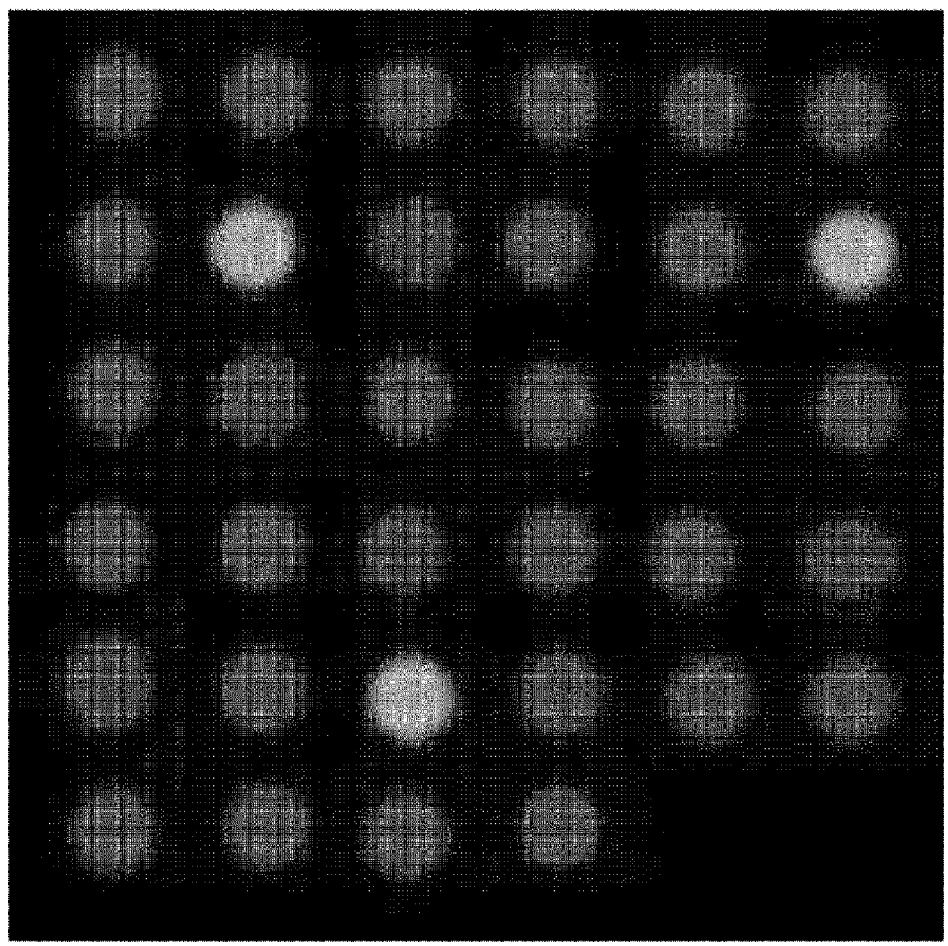
FIG. 8 is a fluorescent image of an array illustrating the analysis of IL17 and IL17RA in terms of proteins, mRNAs, and DNA mutation and methylation after partial double-stranded nucleic acids are formed using oligonucleotides and converted into complete double-stranded nucleic acids, followed by performing PCR on the double-stranded nucleic acids in the presence of signal primers and then hybridizing the labeled PCR products as target probes with capture probes immobilized on the array.

In FIG. 8, the fluorescent intensities of spots vary depending on the properties of the double strands formed between the capture probes and the labeled target probes, and are determined by the signals of the labeled target probes in the spots consisting of single capture probes.

Together with the base sequences of the target probes, prepared from PCR amplicons of target nucleic acids of biomolecules, the base sequences of the capture probes affixed on the array determine the stability of the double strands between the target single-stranded nucleic acids and the capture single-stranded nucleic acids. In addition, the amount of the labeled target probes in each spot on the array has an influence on the fluorescent intensity.

Hence, the fluorescent intensities in FIG. 8 represent the amounts of the target probes while the amounts of the labeled target probes account for the levels of the biomolecules corresponding to the target nucleic acids in the biological sample.

When target probes were prepared from target nucleic acids isolated from control and test samples using signal primers labeled with different markers, particularly with Cy3 for the control and Cy5 for the test sample, the color spectra of blue-yellow-red given to the spots appear, reflecting various ratios between the Cy-3-labeled target probes and the Cy-5-labeled target probes, both being hybridized with the capture probes on the chip. The color intensity detected at a specific spot accounts for the profiles of specific biomolecules present in the control and the test sample.

For nucleic acid mutation analysis, the color spectrum of a spot can convey information about the mutation of a specific gene corresponding to the target nucleic acid applied to the spot. An amplicon is produced only when the upstream oligonucleotide is perfectly complementary to the mutant sequence of a predetermined mutant region of the target nucleic acid, and the target probe is generated using it as a template. Therefore, the analysis of color spectra acquired for spots can show the binding intensity at the spots, identifying the mutation of a specific gene in the biological sample. In FIG. 8, for example, spots appear red due to the Cy5 label, indicating the existence of SNPs corresponding to capture probes prepared with the signal primer P2 in the biological sample.

Also, the color spectra can be used to examine whether or not DNA is methylated. In full consideration of the fact that the signal primer P1 for the methylation-specific upstream oligonucleotide and the signal primer P2 for non-methylation-specific upstream oligonucleotide are labeled with Cy3 and Cy5, respectively, the cytosine at position 144 of the IL17 promoter of the sample was observed to be methylated, as the spot for methylated IL17 appears blue.

Example 10: Analysis of Biomolecule Including Extracellular Molecules of *E. coli*

11-1. Preparation of Oligonucleotide for Analysis of AmpR Gene

Upstream and downstream oligonucleotides for use in analyzing the AmpR gene of pUC19 were synthesized according to Formulas IV and V, respectively (Bioneer, Korea).

TABLE 6

Oligonucleotides for Analysis of Amp$^R$ Gene

| Oligo-nucleotide | Base Sequence (5'→3') | SEQ ID NO. |
|---|---|---|
| Upstream Oligo-nucleotide (wild-type) | 5-GCAGCACTGCATAATTCTCTTACTGTCATG-3 | 168 |
| Upstream Oligo-nucleotide (mutant) | 5-GCAGCACTGCATAATTCTCTTACTGTCATA-3 | 169 |
| Downstream Oligo-nucleotide | 5-CCATCCGTAAGATGCTTTTCTGTGACTGGT-3 | 170 |

10-2. Construction of Analysis Ligand for Cell Surface Molecule

The single-stranded nucleic acids binding to *E. coli* (Korean Patent No. 10-0730359), proposed by the present inventors, have the base sequences listed in Table 7. Based on these sequences, biotinylated, single-stranded nucleic acid ligands and biotinylated oligonucleotides were designed according to Formula I, with reference to sequences of Tables 1 and 2 (Bioneer, Korea).

TABLE 7

Base Sequences of Aptamers Binding to Cell Surface Molecules of *E. coli*.

| # | Base Sequence (5'→3') | SEQ ID NO. |
|---|---|---|
| 1 | cgcaguuugc gcgcguucca aguucucuca ucacggaaua | 171 |
| 2 | acacugcgug cuuacgacuu cugucccau cauucggcua | 172 |
| 3 | aguucgauga gggugacacc gccaggagug uuugcuagac | 173 |
| 4 | acccgucgau aaugacugaa cuuccucuau cuuaaagggg | 174 |
| 5 | ggguaagggg auguuucugg gauucaagcg ccugauucug | 175 |
| 6 | ucuguauuug uacgcaccga agauaagaga gggaguggau | 176 |
| 7 | caugggcggg ccgcggucua uucgggauua uugcggaucc | 177 |
| 8 | ucagggugug aaguucuucc gcgcuagugg cuuguauguu | 178 |
| 8 | gucggguug caaggcgucg uagcguguau uugugauggu | 179 |
| 10 | gcguaugggc gggucauuag gacaauuuaa ccacucgcga | 180 |
| 11 | auugucugug ugacuagucg gucuagugug ggggagaaga | 181 |
| 12 | uuaccacuga guuaauuugu acggucugcg guguacuuua | 182 |
| 13 | gcuaucaaua uuauagaggc ggucggggua gugucaucgu | 183 |
| 14 | uaggagagcg ggagcugaga acuuagaggc gccgauacac | 184 |
| 15 | gacguauuac aguuaaguug gcgccauucg auuucugauc | 185 |
| 16 | auaccagcuu auucaauuau accagcuuau ucaauuugu | 186 |
| 17 | ccguaagucc ggucuuccuu gcugagucgc ccuuucaggu | 187 |
| 18 | uuggugggga gggccaguua ggucuaauuu ccgacgcgca | 188 |

To 100 µl of each of the biotinylated *E. coli* aptamers (10 µg/µl), avidin (7.2 µg/µl) was added. After incubation at room temperature for 30 min, the biotinylated oligonucleotides (10 µg/µl) were reacted with the aptamers and avidin to form aptamer-avidin-oligonucleotide structures, termed aptamer analysis ligands.

10-3. Isolation of Biomolecule from *E. coli*-Analysis Ligand Complex

*E. coli* was reacted with the aptamer analysis ligand pool, after which the *E. coli*-aptamer analysis ligand complexes thus formed were washed and isolated. From the *E. coli*-analysis ligand complex, total nucleic acids including plasmid pUC19 and single-stranded nucleic acids bound to the surface of *E. coli* were extracted. The total nucleic acids were used in the same manner as in Example 5 to prepare target DNA. The target DNA was labeled and amplified in the same manner as in Example 6, followed by conducting analysis on an array constructed in Example 7. Profiles of *E. coli* surface molecules were obtained, and the AmpR gene was identified.

INDUSTRIAL APPLICABILITY

As described above, biomolecules from biological samples can be assayed to determine their biological significance and can be detected at high fluorescent sensitivity through a single assay using the oligonucleotides of the present disclosure. Thus, the method according to the present disclosure allows for the analysis of various biomolecules in a single assay, with the consequent determination of difference in phenotype change, sensitivity to disease, responsiveness to drugs, etc. between persons, whereby a great contribution can be made to overcoming human disease. In addition, the method can find economically advantageous applications in the medical industry.

What is claimed is:

1. A method for simultaneously analyzing a target protein and a target nucleic acid in a biological sample, comprising:
   (a) (i) reacting the target protein of the biological sample with an analysis ligand and forming a target protein-analysis ligand complex, the analysis ligand consisting of a ligand binding specifically to the target protein, and an oligonucleotide linked to the ligand, and
   (ii) producing a hybridization complex by hybridizing the target nucleic acid of the biological sample with an upstream oligonucleotide and a downstream oligonucleotide which are perfectly complementary to an upstream site and a downstream site of the target nucleic acid respectively, and making a double-stranded nucleic acid by extending a region between the upstream oligonucleotide and the downstream oligonucleotide on the hybridization complex, wherein the double-stranded nucleic acid comprises an extended nucleic acid strand which is complementary to the target nucleic acid, the upstream oligonucleotide and the downstream oligonucleotide;
   (b) making a mixture of the target protein-analysis ligand complex and the double-stranded nucleic acid; and
   (c) simultaneously analyzing the target protein and the target nucleic acid in the biological sample by detecting the oligonucleotide of the target protein-analysis ligand complex and the double-stranded nucleic acid, simultaneously, in the mixture of step (b).

2. The method of claim 1, wherein the target nucleic acid is a nucleic acid selected from the group consisting of genomic DNA, genomic DNA treated with sodium bisulfite, and cDNA obtained from RNA by reverse transcription.

3. The method of claim 1, wherein the target nucleic acid is a wild-type target nucleic acid, a mutant target nucleic acid, or a methylated target nucleic acid.

4. The method of claim 1, wherein the ligand is an antibody or an aptamer.

5. The method of claim 1, wherein said detecting the oligonucleotide of the target protein-analysis ligand complex and the double-stranded nucleic acid in step (c) is carried out by:
   (c-1) producing an amplicon of the oligonucleotide of the target protein-analysis ligand complex and an amplicon of the double-stranded nucleic acid by amplifying the oligonucleotide of the target protein-analysis ligand complex and the double-stranded nucleic acid simultaneously in the mixture; and (c-2) simultaneously detecting the amplicon of the oligonucleotide of the target protein-analysis ligand complex and the amplicon of the double-stranded nucleic acid.

6. The method of claim 5, wherein step (c-1) is conducted with a pair of a forward primer and a backward primer, and the oligonucleotide of the target protein-analysis ligand complex and the double-stranded nucleic acid have common regions to which the forward primer and the backward primer respectively bind.

7. The method of claim 5, wherein,
the oligonucleotide of the target protein-analysis ligand complex has a region that is used for discriminating the target protein,
the double-stranded nucleic acid has a region that is used for discriminating the target nucleic acid, and
step (c-2) is conducted by detecting the region of that is used for discriminating the target protein in the oligonucleotide of the target protein-analysis ligand complex and the region that is used for discriminating the target nucleic acid in the double-stranded nucleic acid simultaneously.

8. The method of claim 6, wherein at least one of the forward primer and the backward primer comprises a detectable marker capable of generating a detection signal, and step (c-2) is conducted by detecting the detection signal generated from the detectable marker detection signal.

9. The method of claim 8, wherein the primer which comprises the detectable marker is the forward primer.

10. The method of claim 1, wherein
the oligonucleotide of the analysis ligand in the target protein-analysis ligand complex has a region to which a forward primer binds, a region to which a backward primer binds, and a region used for discriminating the target protein, located between the region to which the forward primer binds and the region to which the backward primer binds,
the upstream oligonucleotide has a region to which the forward primer binds, and a downstream region that hybridizes specifically to the target nucleic acid,
the downstream oligonucleotide has a region that recognizes and hybridizes with the target nucleic acid, and a downstream region to which a backward primer binds, wherein, in the double stranded nucleic acid, the downstream oligonucleotide hybridizes to a site of the target nucleic acid downstream from a site of the target nucleic acid to which the upstream oligonucleotide hybridizes,
a region used for discriminating the target nucleic acid in the upstream oligonucleotide is located between a region of the upstream oligonucleotide to which the forward primer binds and a region of the upstream oligonucleotide which hybridizes to the target nucleic acid or a region used for discriminating the target nucleic acid in the downstream oligonucleotide, is located between a region of the downstream oligonucleotide which hybridizes to the target nucleic acid and a region of the downstream oligonucleotide to which the backward primer binds,
the oligonucleotide of the target protein-analysis ligand complex, and the upstream oligonucleotide and the downstream oligonucleotide of the double-stranded nucleic acid have the same sequence region to which the forward primer binds and the same sequence region to which the backward primer binds, whereby,
said detecting the oligonucleotide of the target protein-analysis ligand complex and the double-stranded nucleic acid in step (c) is carried out by (c-i) obtaining an amplicon of the oligonucleotide of the target protein-analysis ligand complex and an amplicon of the double-stranded nucleic acid by simultaneously amplifying the oligonucleotide of the target protein-analysis ligand complex and the double-stranded nucleic acid of the mixture in the presence of the forward primer and the backward primer; and (c-ii) simultaneously detecting the region used for discriminating the target protein in the amplicon of the oligonucleotide of the target protein-analysis ligand complex and the region used for discriminating the target nucleic acid in the amplicon of the double-stranded nucleic acid.

11. The method of claim 10, wherein the forward primer is a primer comprising a detectable marker capable of generating a detection signal whereby step (c-ii) is achieved by detecting the detection signal from the detectable marker in the amplicon of the oligonucleotide of the target protein-analysis ligand complex and detecting the detection signal from the detectable marker in the amplicon of the double-stranded nucleic acid, wherein the detectable marker of the forward primer used for amplifying the oligonucleotide of the target protein-analysis ligand complex and the detectable marker of the forward primer used for amplifying the double-stranded nucleic acid are different and produce different detection signals.

12. The method of claim 11, wherein the target nucleic acid is a nucleic acid selected from RNA, cDNA, and genomic DNA, the cDNA being reversely transcribed from RNA.

13. The method of claim 11, wherein step (c-ii) further comprises:
applying the amplicon of the oligonucleotide of the target protein-analysis ligand complex and the amplicon of the double-stranded nucleic acid to a microarray onto which a capture probe having a sequence complementary to the region used for discriminating the target protein in the amplicon of the oligonucleotide of the target protein-analysis ligand complex and a capture probe having a sequence complementary to the region used for discriminating the target nucleic acid in the amplicon of the double-stranded nucleic acid are immobilized and inducing hybridization complexes; and
removing the amplicon of the oligonucleotide of the target protein-analysis ligand complex and the amplicon of the double-stranded nucleic acid that are not hybridized to the microarray;
wherein said detecting the detection signal from the detectable marker in the amplicon of the oligonucleotide of the target protein-analysis ligand complex and said detecting the detection signal from the detectable marker in the amplicon of the double-stranded nucleic acid comprises detecting the detection signal from the detectable marker in the amplicon of the oligonucleotide of the target protein-analysis ligand complex hybridized to the microarray and the detection signal from the detectable marker in the amplicon of the double-stranded nucleic acid hybridized to the microarray.

* * * * *